US008315805B2

(12) United States Patent
Opalsky et al.

(10) Patent No.: US 8,315,805 B2
(45) Date of Patent: Nov. 20, 2012

(54) SYSTEMS AND METHODS FOR TESTING A BIOLOGICAL SAMPLE

(75) Inventors: David Opalsky, San Diego, CA (US); Ping Yip, San Diego, CA (US); Kishorchandra Bhakta, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 200 days.

(21) Appl. No.: 10/128,680

(22) Filed: Apr. 22, 2002

(65) Prior Publication Data

US 2003/0033091 A1 Feb. 13, 2003

Related U.S. Application Data

(63) Continuation-in-part of application No. 09/839,629, filed on Apr. 20, 2001, now abandoned.

(51) Int. Cl.
*G06F 19/00* (2011.01)
*G01N 24/00* (2006.01)

(52) U.S. Cl. ........................................................ 702/19

(58) Field of Classification Search .................. 702/19, 702/22, 28; 422/65, 67; 435/6; 436/43, 436/47, 181, 94; 424/94.1; 91/2; 250/281, 250/288; 706/15
See application file for complete search history.

(56) References Cited

U.S. PATENT DOCUMENTS

| | | | | |
|---|---|---|---|---|
| 4,076,982 A | 2/1978 | Ritter et al. | ..................... | 250/288 |
| 4,826,360 A | 5/1989 | Iwasawa et al. | ..................... | 406/51 |
| 4,851,018 A | 7/1989 | Lazzari et al. | ..................... | 55/356 |
| 5,122,342 A | 6/1992 | McCulloch et al. | ............. | 422/65 |
| 5,175,430 A | 12/1992 | Enke et al. | ..................... | 250/282 |
| 5,247,175 A | 9/1993 | Schoen et al. | ................. | 250/281 |
| 5,273,718 A | 12/1993 | Sköld et al. | ..................... | 422/101 |
| 5,363,885 A | 11/1994 | McConnell et al. | .............. | 141/1 |
| 5,440,119 A | 8/1995 | Labowsky | ..................... | 250/282 |
| 5,453,613 A | 9/1995 | Gray et al. | ..................... | 250/281 |
| 5,498,545 A | 3/1996 | Vestal | ............................. | 436/47 |
| 5,539,083 A | 7/1996 | Cook et al. | ..................... | 530/333 |
| 5,547,835 A | 8/1996 | Köster | ............................... | 435/6 |
| 5,605,798 A | 2/1997 | Köster | ............................... | 435/6 |
| 5,622,824 A | 4/1997 | Köster | ............................... | 435/6 |
| 5,691,141 A | 11/1997 | Köster | ............................... | 435/6 |
| 5,777,324 A | 7/1998 | Hillenkamp | ..................... | 250/288 |
| 5,802,323 A | 9/1998 | Bujanos et al. | ............... | 395/287 |
| 5,807,522 A | 9/1998 | Brown et al. | ..................... | 422/50 |
| 5,851,765 A | 12/1998 | Köster | ............................... | 435/6 |
| 5,869,240 A * | 2/1999 | Patterson | ......................... | 435/6 |
| 5,872,003 A | 2/1999 | Köster | ......................... | 435/283.1 |
| 5,885,841 A | 3/1999 | Higgs, Jr. et al. | ............... | 436/89 |
| 5,900,481 A | 5/1999 | Lough et al. | ................. | 536/55.3 |
| 5,928,906 A | 7/1999 | Köster et al. | ................. | 435/91.2 |
| 5,928,952 A | 7/1999 | Hutchins et al. | ............... | 436/50 |
| 5,985,214 A | 11/1999 | Stylli et al. | ..................... | 422/65 |
| 6,017,693 A | 1/2000 | Yates, III et al. | ................. | 435/5 |
| 6,022,688 A | 2/2000 | Jurinke et al. | ..................... | 436/6 |
| 6,024,925 A | 2/2000 | Little et al. | ..................... | 422/100 |
| 6,043,031 A | 3/2000 | Köster et al. | ..................... | 435/6 |
| 6,060,022 A | 5/2000 | Pang et al. | ......................... | 422/65 |
| 6,074,823 A | 6/2000 | Köster | ............................... | 435/6 |
| 6,110,426 A | 8/2000 | Shalon et al. | ................. | 422/68.1 |
| 6,111,251 A | 8/2000 | Hillenkamp | ..................... | 250/288 |
| 6,132,685 A | 10/2000 | Kercso et al. | ................. | 422/104 |
| 6,132,724 A | 10/2000 | Blum | ......................... | 424/195.1 |
| 6,133,436 A | 10/2000 | Köster et al. | ................. | 536/24.3 |
| 6,140,053 A | 10/2000 | Köster | ............................... | 435/6 |
| 6,146,854 A | 11/2000 | Köster et al. | ................. | 435/1.1 |
| 6,147,344 A | 11/2000 | Annis et al. | ..................... | 250/281 |
| 6,207,370 B1 | 3/2001 | Little et al. | ..................... | 435/6 |
| 6,225,450 B1 | 5/2001 | Köster | ............................... | 6/22.1 |
| 6,675,104 B2 * | 1/2004 | Paulse et al. | ..................... | 702/22 |
| 2001/0023419 A1 * | 9/2001 | Lapointe et al. | ............... | 706/15 |
| 2001/0055811 A1 | 12/2001 | Hillenkamp | ..................... | 436/43 |
| 2002/0009394 A1 * | 1/2002 | Koster et al. | ..................... | 422/65 |
| 2002/0040130 A1 | 4/2002 | Braun | ......................... | 536/23.1 |
| 2002/0109085 A1 | 8/2002 | Hillenkamp et al. | ......... | 250/288 |

FOREIGN PATENT DOCUMENTS

| | | |
|---|---|---|
| EP | 0596205 | 5/1994 |
| EP | 2749662 A1 | 12/1997 |
| JP | A-2000-131285 | 5/2000 |
| JP | A-2000-228999 | 8/2000 |
| JP | A-2000-316560 | 11/2000 |
| JP | A-2000-516727 | 12/2000 |
| WO | 9315407 | 8/1993 |
| WO | 9416101 | 7/1994 |
| WO | 9421822 | 9/1994 |
| WO | 9629431 | 9/1996 |
| WO | 9708306 | 3/1997 |
| WO | WO 97/29447 | 8/1997 |
| WO | 9737041 | 10/1997 |
| WO | 9742348 | 11/1997 |
| WO | 9743617 | 11/1997 |

(Continued)

OTHER PUBLICATIONS

Ikegami et al. (J Biolumin Chemilumin, vol. 10 p. 219-27, 1995).*
Wu et al. (Anal. Chem., vol. 69, p. 3767-3771, 1997).*
Griffin et al. (Anal. Chem., vol. 72, p. 3298-3302, 2000).*
Egholm et al., "PNA hybridizes to complementary oligonucleotides obeying the Watson-Crick Hydrogen-bonding rules", *Nature*, 365:566-568 (1993).
Leushner, et al., "Automated mass spectrometry: a revolutionary technology for clinical diagnostics." Molecular Diagnostics, vol. 5, No. 4, Dec. 2000, pp. 341-348.

(Continued)

*Primary Examiner* — Lori A Clow
(74) *Attorney, Agent, or Firm* — Grant Anderson LLP

(57) ABSTRACT

Systems and methods for testing samples, particularly biological samples are provided. The system includes an instrument for detecting molecules in samples, and a processor that communicates with the instrument to provide results-based control of the instrument to effect assay-based judging. For example, a system, including software, is provided that directs and performs assays such as diagnostic assays that employ a mass spectrometer. The output of the system, rather than a mass spectrum or other raw data form, is the diagnostic outcome, such as a genotype.

36 Claims, 10 Drawing Sheets

FOREIGN PATENT DOCUMENTS

| WO | 9812734 | 3/1998 |
|---|---|---|
| WO | 9820019 | 5/1998 |
| WO | 9820020 | 5/1998 |
| WO | 9820166 | 5/1998 |
| WO | 9833808 | 8/1998 |
| WO | WO 98/59362 | 12/1998 |
| WO | 9912040 | 3/1999 |
| WO | 9931278 | 6/1999 |
| WO | 9957318 | 11/1999 |
| WO | 0009394 | 2/2000 |
| WO | 0040130 | 7/2000 |
| WO | 0055811 | 9/2000 |
| WO | 0056446 | 9/2000 |
| WO | 0060361 | 10/2000 |
| WO | 0109085 | 2/2001 |
| WO | WO 01/16860 | 3/2001 |
| WO | 0225567 | 3/2002 |

OTHER PUBLICATIONS

Partial European Search Report in related European Application EP-02-76-4326 completed, Jul. 16, 2007. Received, Jul. 26, 2007.
Pusch, et al., "Genotools SNP Manager: A 1-66 New Software for Automated High-Throughput MALDI-TOFF Mass Spectrometry SNP Genotyping," Biotechniques, Informa Life Sciences Publishing, Westborough, MA, vol. 30, No. 1, Jan. 2001, pp. 210-215.
Suckau, et al., "Automatic acquisition of MALDI-TOFF mass spectra," Analysis Magazine, vol. 26, No. 10, 1998, pp. 36-40.
Jensen, "Mass spectrometric identification and microcharacterization of proteins from electrophoretic gels: strategies and applications," Proteins; Suppl, 1998, vol. 2, p. 74-89.
Badger et al., "New features and enhancements in the X-PLOR computer program", Proteins, 35(1):25-33 (1999).
Braun et al., "Improved analysis of microsatellites using mass spectrometry", Genomics, 46(10):18-23 (1997).
Database WPI, Derwent publication # 011635345 citing International Patent Application WO 9747974 of the parent French Patent Application FR 2,749,662, WO DOC-1997.
Goldmacher et al., "Photoactivation of toxin conjugates", Bioconj. Chem., 3:104-107 (1992).
Hazum et al., "A photocleavable protecting group for the thiol function of cysteine", Pept., Proc. Eur. Pept. Symp., 16th, Brunfeldt, K (ed), pp. 105-110 (1981).
Hinton et al., "The application of robotics to fluorometric and isotopic analyses of uranium", Laboratory Automation & Information Management, NL, Elsevier Science publishers BV., Amsterdam, vol. 21 No. 2/03, pp. 223-227, Dec. 1, 1993.
Instrumentation; Bar code systems, including one and two dimensional bar codes, readable and readable/writable codes and systems; Datalogic S.p.A. of Italy ("Datalogic") located at http://www.datalogic.com, 1999.
Instrumentation; Dynabeads, streptavidin-coated magnetic beads; from Dynal, Inc. Great Neck, NY and Oslo Norway, 1999.
Instrumentation; "MJ Microseal" plate sealer; Thermal Cycler Accessories: Sealing Options, Sealing Products, MJ Research, located at http://www.mjresearch.com/html/consumables/ealing/sealing_products.html, 1999.
Instrumentation; "Multimek 96" automated pipettor; Beckman Coulter, Inc. located at http://www.coulter.com, Sep. 8, 1999.
Instrumentation; "Model CRS A 255" robot "Digital Servo Gripper" "Plate Cube" system. "lid parking station" "shaker" Robocon Labor-und Industrieroboter Ges.m.b.H of Austria ("Robocon"), 1999.
Instrumentation; "Nano-Plotter" from GeSiM, Germany, located at http:/www.gesim.de/np-intro.htm, 2000.
Instrumentation; "Genesis 200/8" (200 cm with including an 8-tip arm) liquid handling systems; Tecan AG of Switzerland ("Tecan"), TECAN Products for Diagnostics and Life Science, located at http://www.tecan.ch/index.htm, 1999.
IUPAC-IUB Commission of Biochemical Nomenclature, "Abbreviated Nomenclature of Synthetic Polypeptides (Polymerized Amino Acids)", Biochemistry, 11(5):942-944 (1972).
Jensen et al., "Mass Spectrometric Identification and Microcharacterization of Protein From Electrophoretic Gels: Strategies and Applications", Proteins: Structure, Function, and Genetics Suppl., 2:74-89 (1998).
Little et al., "MALDI on a chip: analysis of arrays of low-femtomole to subfemtomole quantities of synthetic oligonucleotides and DNA diagnostic products dispensed by a piezoelectric pipet", Anal. Chem., 69:4540-4546 (1997).
Little et al., "Identification of apolipoprotein E polymorphisms using temperature cycled primer oligo base extension and mass spectrometry", Eur. J. Clin. Chem. Clin. Biochem., 35(7):545-548(1997).
Nilges et al., "Automated NOESY interpretation with ambiguous distance restraints: the refined NMR solution structure of the pleckstrin homology domain from β-spectrin", J. Mol. Biol., 269:408-422 (1997).
Senko et al., "Automated Assignment of Charge States from Resolved Isotopic Peaks for Multiply Charged Ions", J. Am. Soc. Mass. Spectrom., 6:52-56 (1995).
Senter et al., "Novel photocleavable protein crosslinking reagents and their use in the preparation of antibody-toxin conjugates", Photochem. Photobiol., 42:231-237 (1985).
Sequenom Advances the Industrial Genomics Revolution with the Launch of Its DNA MassArrayJAutomated Process Line, Press Release: Sep. 28, 1998, http://www.sequenom.com/pressrelease.htm.
Sequenom: Technologies and Tools, located at http://www.sequenom-san.com/tech/tools.html, dated Aug. 29, 1999.
Tammen et al., "Proteolytic cleavage of glucagon-like peptide-1 by pancreatic β cells and by fetal calf serum analyzed by mass spectrometry", J. Cromatogr. A, 852:285-295 (1999).
Thompson, "Fitting robots with white coats", Laboratory Automation and Information Management, 31:173-193 (1996).
Traini et al., "Towards an automated approach for protein identification in proteome projects", Electrophoresis, 19:1941-1949 (1998).
Wang et al., "Allene $\gamma_9$ and $\gamma_{10}$: low-temperature measurements of line intensity", J. Mol. Specirosc., 194(20):256-268 (1999).
Weiler et al., "Hybridisation based DNA screening on peptide nucleic acid (PNA) oligomer arrays", Nucleic Acids Res., 25:2792-2799 (1997).
Yates, III, Special Feature: Tutorial, "Mass Spectrometry and the Age of the Proteome", J. Mass. Spect., 33:1-19 (1998).
Yen et al., "Synthesis of water-soluble copolymers containing photocleavable bonds", Makromol. Chem., 190:69-82 (1989).

* cited by examiner

SYSTEMS AND METHODS FOR TESTING A BIOLOGICAL SAMPLE

RELATED APPLICATIONS

This application is a continuation-in-part of U.S. application Ser. No. 09/839,629, entitled "SYSTEM AND METHOD FOR TESTING A BIOLOGICAL SAMPLE" to David Opalsky, Ping Yip and Kishorchandra Bhakta, filed Apr. 20, 2001 now abandoned. The subject matter of this application is incorporated herein in its entirety.

TECHNICAL FIELD

Mass spectrometry-based methods, products and systems for testing samples, such as biological samples are provided. In one example, a system having a processor is used to implement a disclosed testing method.

BACKGROUND

Instruments, such as the mass spectrometer, are now routinely used to assist in identifying components of a biological sample. In particular, the MALDI-TOF (matrix-assisted desorption ionization time-of-flight) mass spectrometer has proven useful for making biological determinations, such as genotyping or identifying single nucleotide polymorphisms.

The MALDI TOF mass spectrometer generally operates by directing an energy beam at a target spot on a biological sample. The energy beam disintegrates the biological material at the target spot, with the disintegrated component material hurled toward a measurement module. The lighter component material arrives at the measurement module before the heavier component material. The measurement module captures the component material, and generates a data set indicative of the mass of the component material sensed. Typically, the data set is generated as a two dimensional spectrum, with the x-axis representing a mass number, and the y-axis representing a quantity number.

The data, which is often presented as a data spectrum, typically has peaks positioned on a generally exponentially decaying baseline. Each peak ideally should represent the presence of a component of the biological sample. Unfortunately, due to chemical and mechanical limitations, the data spectrum is replete with noise, so an accurate determination of biological components can be challenging. Indeed, it takes an experienced operator to accurately read and interpret a data spectrum. Efforts of even the best trained human operator can suffer from inaccuracies and errors. Since the results derived from data spectra often are used in health care decisions, mistakes can be devastating. Therefore, operators are trained to make a determination only when certain of the result. In such a manner, a great number of tests result in no-calls, where the operator cannot clearly identify a data result.

Accordingly, the use of mass spectrometers risks an unacceptably large number of inaccurate calls, if the operator is applying a rather loose standard to the data spectrum. Alternatively, the use of mass spectrometers becomes highly inefficient if the operator discards a large number of tests due to an inability to confidently make a call.

To assist the operator in making calls, the mass spectrometer can provide a level of data filtering. Typically, the data filtering attenuates a set magnitude of noise, thereby more conspicuously exposing valid peaks. Such a filtering technique actually can mask important valid peaks, resulting in an incorrect analysis.

Modern trends in biotechnology are taxing the capabilities of instruments such as mass spectrometers and their operators. For example, mass spectrometers are now used to identify single nucleotide polymorphisms (SNPs). SNPs can produce only slight peaks on the data spectrum, which are easily missed by an operator or buried in background noise. Further, mass spectrometers are also used for multiplexing, where multiple gene reactions can be performed in a single sample. In such a manner, the resulting peaks can be smaller, more difficult to identify, and there can be more combinations of false readings. With such complicated data spectra it is becoming more difficult for an operator to confidently determine if a valid peak exists for a particular genetic component.

In addition, the mass spectrometer data collection process can be unnecessarily prolonged for a sample. This can occur, for example, when a "raster" technique is used to repeatedly acquire spectrum output from a sample until output indicates satisfactory data was received. Inaccurate analysis of spectrum data can cause satisfactory output to be unrecognized, resulting in unnecessary rastering to continue collecting additional data.

As tests become more complex and the demand for high throughput outputs increases, the mass spectrometer can provide data spectra that are difficult for an operator to interpret. Even under the best of conditions, the operator can make identifications where a call should not have been made, or can discard good acquired data because of perceived ambiguity. Accordingly, there exists a need for a more efficient and accurate method and system for identifying samples, including biological sample. Therefore, among the objects herein, it is an object herein to provide methods, products and systems to meet such need.

SUMMARY

Testing systems and methods that exhibit efficient and accurate biological identification of instrument output, such as mass spectrometer output, are provided. The systems and methods provided herein employ assay-based judging, in the ultimate biological significance of the data are feedback to the data acquisition routines and instrument, to improve the performance of biological assays, including those involving multiplex assays. In multiplex formats, each assay is treated as an individual test generating a separate result. In the systems herein and in accord with the methods provided herein, biological results are displayed in real time and on the user interface of a test instrument, such as a mass spectrometry control system. The methods and systems herein are designed to provide high speed and high throughput tests; only needed data are acquired thereby eliminating time spent blindly acquiring unnecessary data.

In particular, systems and methods for implementing the systems for obtaining and displaying results of assays, generally real-time (RT) results, are provided. The systems and methods are ideal for high throughput formats, in which a plurality of samples, typically at least about 96, 384, 1534 and higher numbers of samples, are tested. The samples can be biological samples and can include identical samples on which a plurality of tests are performed and samples from a plurality of different sources in which one or a plurality of tests are performed or any combination thereof. The systems include an instrument, such as a mass spectrometer, NMR spectrometer, gas chromatograph, high pressure liquid chromatograph (HPLC), or combinations thereof, for data acquisition, and a processor. The process directs operation of the instrument and the assays performed thereby and includes software (routines) for data collection (data acquisition), and data processing routines to assess the collected data. Methods employing the systems are provided. In the systems and methods provided herein, the results of the tests performed by the assays and the assays, i.e., that data collection routine and data processing routine, are integrated so that the real-time results are used in directing the data acquisition.

Mass spectrometry systems are also provided. These systems use biology-based results to control data acquisition in the mass spectrometer thereby significantly improving call efficiency and increasing the instrument throughput. The exemplified system includes highly optimized versions of calling algorithms with a streamlined interface to a database to store the results, such as genotyping results. As part of the optimization, a well-defined programming interface that controls the dialog between the data acquisition component and the biological-calling component of spectra analysis was developed. The interface is flexible and modular to allow modification of the calling algorithms. The interface that controls the dialogue between the data acquisition component and the biological calling component is provided.

It has been observed that calling efficiency can be improved by over 50% using the techniques provided herein. The improvement has been found to depend on the quality of the assay and the level of multiplexing.

Systems for data acquisition and analysis are provided. The systems include a computer-directed data collection routine; and a computer-directed data processing routine. The data collection and data processing routines are integrated so that tests are performed on a sample and the output from an instrument that includes such integrated software is a diagnosis. Thus, for example, the software, systems and methods provided herein converts a mass spectrometer into a detector is a system that displays biological results, particularly, real time biological results, such as a genotype and allelic frequency.

Methods for testing samples, such as biological samples, are provided. These methods use a testing system that includes a processor and an instrument that is configured to acquire data from a sample, such as a biological sample. In performing the testing method, the instrument acquires data from the sample, and the processor compares the acquired data to predefined data criteria. Responsive to comparing the acquired data to the data criteria, the instrument can be adjusted, and another data set acquired. In one disclosed example of the testing system, a mass spectrometer acquires data from a biological sample. The acquired data are compared to predefined spectrum criteria. Responsive to the comparison, the mass spectrometer can be directed to resample the biological sample or proceed to another sample.

Advantageously, the disclosed methods and systems for testing samples, such as a biological sample, provide automated control of an instrument, such as a mass spectrometer, a gas chromatograph, electrophoresis apparatus, NMR instruments and other instruments and combinations thereof, and permit direct readout of results of a test rather than readout of instrument output, such as a mass spectrum. More particularly, the testing method provides a highly accurate determination of a sample with minimal manual intervention. Accordingly, samples can be identified and diagnostic tests performed with a high degree of precision, speed, and accuracy.

Software and computer-readable media containing such software are provided. Processors and diagnostic systems that include such software and instruments that employ the software to direct processing of samples, such as mass spectrometric analysis of molecules in the samples are provided. The software provided herein converts an instrument, such as a mass spectrometer, into a detector that displays biological results, particularly, real time biological results, such as a genotype and/or allelic frequency. Instruments, such as a mass spectrometer, that displays biological results are provided.

DETAILED DESCRIPTION

A. Definitions

Figure 1:
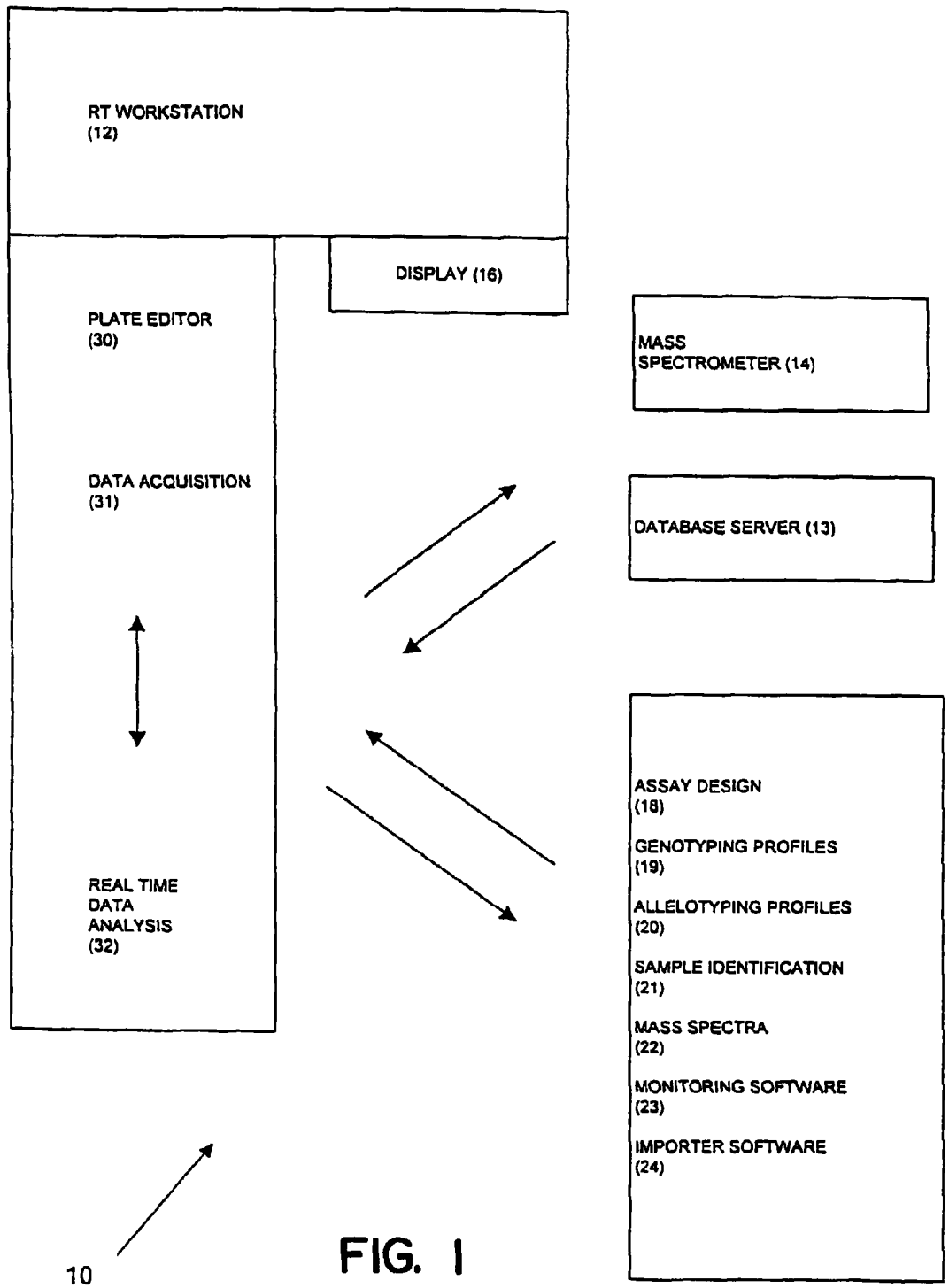
FIG. 1 is a block diagram of a testing system provided herein.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Among the issued patents and published international applications incorporated by reference and that describe methods that can be adapted for use with the methods and systems provided herein, are: U.S. Pat. Nos. 5,807,522, 6,110,426, 6,024,925, 6,133,436, 5,900,481, 6,043,031, 5,605,798, 5,691,141, 5,547,835, 5,872,003, 5,851,765, 5,622,824, 6,074,823, 6,022,688, 6,111,251, 5,777,324, 5,928,906, 6,225,450, 6,146,854, 6,207,370, U.S. application Ser. No. 09/663,968, International PCT application No. WO 99/12040, WO 97/42348, WO 98/20020, WO 98/20019, WO 99/57318, WO 00/56446, WO 00/60361 and WO 02/25567. These patents and publications describe a variety of mass spectrometric analytical methods, substrates and matrices used in mass spectrometric analyses, and related methods and apparatus, including pin tools and other dispensing systems. It is intended that the methods, products and systems provided herein can be adapted for use with the methods and products described and used in these patents and patent applications as well as other such methods that employ instruments for detection of molecules and computer-directed assays, and are particularly suitable for use in high throughput formats. Other intended uses include any methods and assays that have an instrument for data acquisition and that employ data-typing analyses.

As used herein, assay-based judging refers to a method in which decisions regarding further sampling or testing of the assays are based on the ultimate results, the biological significance (i.e., the biological result such as a genotype), rather than specific results of data acquisition by an instrument (and related software), such as a mass spectrum or chromatograph, from an instrument.

As used herein, assay results refer to the output from a particular protocol, such as for example, a mass spectrum for molecules in a sample.

As used herein, ultimate results are the actual determination, such as a genotype or other diagnosis, achieved by the sampling.

As used herein, a programming interface refers to specifications for programming communications, such as application programming interfaces (API's) and communication protocols that permit data exchange and transfer between programs and devices, such as instruments. These include, for example, API's for the Microsoft Windows® operating system and for TCP/IP communications.

As used herein, "good" with reference to data and/or results means that the skill artisan would use the data or the results to reach a conclusion or would not discard such data or results. Whether data or results are good is a function of the particular data and/or results and will be apparent to the skilled artisan familiar with such data and/or results and the related technologies.

As used herein, a call refers to identification of a data result, such as a genotype or a diagnosis or allotype.

As used herein, an assay design refers to the instructions for effecting a protocol to perform an assay, such as a diagnostic test, including those involving genotyping.

As used herein, real-time (RT) control refers to the ability of a RT workstation to receive data from the data acquisition instrument, such as a mass spectrometer, to process the data and provide command direction to the instrument, such as a mass spectrometer, in an automated manner.

As used herein, a data collection routine refers to a process, that can be embodied in software, that controls data acquisition by an instrument, such as a mass spectrometer, refers to a process, typically an automated computer-controlled process, that directs the instrument in collection of data and determines if output data, such as mass data from a mass spectrometry, is of suitable quality for analysis. For example, the data collection routine can assess signal-to-noise ratios.

As used herein, a data processing routine refers to a process, that can be embodied in software, that determines the biological significance of acquired data (i.e., the ultimate results of the assay). For example, the data processing routine can make a genotype determination based upon the data collected. In the systems and methods herein, the data processing routine also controls the instrument and/or the data collection routine based upon the results determined. The data processing routine and the data collection routines are integrated and provide feedback to operate the data acquisition by the instrument, and hence provide the assay-based judging methods provided herein.

As used herein, "sample" refers to a composition containing a material, such as a molecule, to be detected. In an exemplary embodiment, the sample is a "biological sample" (i.e., any material obtained from a living source (e.g. human, animal, plant, bacteria, fungi, protist, virus). The biological sample can be in any form, including solid materials (e.g. tissue, cell pellets and biopsies) and biological fluids (e.g. urine, blood, saliva, amniotic fluid and mouth wash (containing buccal cells)). Solid materials typically are mixed with a fluid. In particular, herein, the sample refers to a mixture of matrix used for mass spectrometric analyses and biological material such as nucleic acids.

As used herein, a "biological sample" refers to material that can be derived from a living source. Such samples include, biomolecules and biopolymers. The molecules can be treated, such as by amplification, cloning and subcloning, and isolation processes prior to assessment.

As used herein, a molecule refers to any molecule or compound that is linked to or contained on or in a well or other indentation on or in a solid support, such as a chip. Typically such molecules are macromolecules or components or precursors thereof, such as peptides, proteins, small organics, oligonucleotides or monomeric units of the peptides, organics, nucleic acids and other macromolecules. A monomeric unit refers to one of the constituents from which the resulting compound is built. Thus, monomeric units include, nucleotides, amino acids, and pharmacophores from which small organic molecules are synthesized.

As used herein, macromolecule refers to any molecule having a molecular weight from the hundreds up to the millions. Macromolecules include peptides, proteins, nucleotides, nucleic acids, and other such molecules that are generally synthesized by biological organisms, but can be prepared synthetically or using recombinant molecular biology methods.

As used herein, a biopolymer includes, but is not limited to, nucleic acids, proteins, polysaccharides, lipids and other macromolecules. Nucleic acids include DNA, RNA, and fragments thereof. Nucleic acids can be isolated or derived from genomic DNA, RNA, mitochondrial nucleic acid, chloroplast nucleic acid and other organelles with separate genetic material or can be prepared synthetically. Thus, the term "biopolymer" is used to mean a biological molecule, including macromolecules, composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein, respectively. The methods and systems herein, though described with reference to biopolymers, can be adapted for use with other synthetic schemes and assays, such as organic syntheses of pharmaceuticals, or inorganics and any other reaction or assay performed on a solid support or in a well in nanoliter or smaller volumes.

As used herein, labels include any composition or moiety that can be attached to or incorporated into nucleic acid that is detectable by spectroscopic, photochemical, biochemical, immunochemical, electrical, optical or chemical means. Exemplary labels include, but are not limited to, biotin for staining with labeled streptavidin conjugate, magnetic beads (e.g., Dynabeads™), fluorescent dyes (e.g., 6-FAM, HEX, TET, TAMRA, ROX, JOE, 5-FAM, R110, fluorescein, texas red, rhodamine, phycoerythrin, lissamine, phycoerythrin (Perkin Elmer Cetus), Cy2, Cy3, Cy3.5, Cy5, Cy5.5, Cy7, FluorX (Amersham), radiolabels, enzymes (e.g., horse radish peroxidase, alkaline phosphatase and others used in ELISA), and colorimetric labels such as colloidal gold or colored glass or plastic (e.g., polystyrene, polypropylene, latex and other supports) beads, a fluorophore, a radioisotope or a chemiluminescent moiety.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials. For purposes herein, biological particles include molecules that are not typically considered macromolecules because they are not generally synthesized, but are derived from cells and viruses.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA, such as peptide nucleic acid (PNA), phosphorothioate DNA, and other such analogs and derivatives or combinations thereof. Thus, as used herein, nucleic acids include DNA, RNA and analogs thereof, including protein nucleic acids (PNA) and mixture thereof. When referring to probes or primers, optionally labeled with a detectable label, such as a fluorescent or radiolabel, single-stranded molecules are contemplated. Such molecules are typically of a length such that they are statistically unique or low copy number (typically less than 5 or 6, generally less than 3 copies in a library) for probing or priming a library. Generally a probe or primer contains at least 14, 16 or 30 contiguous nucleotides from a selected sequence thereof complementary to or identical to a polynucleotide of interest. Probes and primers can be 10, 14, 16, 20, 30, 50, 100 or more nucleic acid bases long.

As used herein, the term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a phophorothioate bond, a thioester bond, or a peptide bond (peptide nucleic acid). The term "oligonucleotide" also is used herein essentially synonymously with "polynucleotide," although those in the art recognize that oligonucleotides, for example, PCR primers, generally are less than about fifty to one hundred nucleotides in length.

Nucleotide analogs contained in a polynucleotide can be, for example, mass modified nucleotides, which allows for mass differentiation of polynucleotides; nucleotides containing a detectable label such as a fluorescent, radioactive, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, which is cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, or other such bond or linkage, and can be extended by a polymerase. Peptide nucleic acid sequences can be prepared using well known methods (see, for example, Weiler et al., *Nucleic acids Res.* 25:2792-2799 (1997)).

A polynucleotide can be a portion of a larger nucleic acid molecule, for example, a portion of a gene, which can contain a polymorphic region, or a portion of an extragenic region of a chromosome, for example, a portion of a region of nucleotide repeats such as a short tandem repeat (STR) locus, a variable number of tandem repeats (VNTR) locus, a microsatellite locus or a minisatellite locus. A polynucleotide also can be single stranded or double stranded, including, for example, a DNA-RNA hybrid, or can be triple stranded or four stranded. Where the polynucleotide is double stranded DNA, it can be in an A, B, L or Z configuration, and a single polynucleotide can contain combinations of such configurations.

As used herein, "oligonucleotide," "polynucleotide" and "nucleic acid" include linear oligomers of natural or modified monomers or linkages, including deoxyribonucleosides, ribonucleotides, α-anomeric forms thereof capable of specifically binding to a target gene by way of a regular pattern of monomer-to-monomer interactions, such as Watson-Crick type of base pairing, base stacking, Hoogsteen or reverse Hoogsteen types of base pairing. Monomers are typically linked by phosphodiester bonds or analogs thereof to form the oligonucleotides. Whenever an oligonucleotide is represented by a sequence of letters, such as "ATGCCTG," it is understood that the nucleotides are in a 5'→3' order from left to right.

Typically oligonucleotides for hybridization include the four natural nucleotides; however, they also can include non-natural nucleotide analogs, derivatized forms or mimetics. Analogs of phosphodiester linkages include phosphorothioate, phosphorodithioate, phosphorandilidate, phosphoramidate, for example. A particular example of a mimetic is protein nucleic acid (see, e.g., Egholm et al. (1993) *Nature* 365: 566; see also U.S. Pat. No. 5,539,083).

As used herein, the term "polypeptide," means at least two amino acids, or amino acid derivatives, including mass modified amino acids and amino acid analogs, that are linked by a peptide bond, which can be a modified peptide bond. A polypeptide can be translated from a polynucleotide, which can include at least a portion of a coding sequence, or a portion of a nucleotide sequence that is not naturally translated due, for example, to its location in a reading frame other than a coding frame, or its location in an intron sequence, a 3' or 5' untranslated sequence, a regulatory sequence such as a promoter. A polypeptide also can be chemically synthesized and can be modified by chemical or enzymatic methods following translation or chemical synthesis. The terms "polypeptide," "peptide" and "protein" are used essentially synonymously herein, although the skilled artisan recognizes that peptides generally contain fewer than about fifty to one hundred amino acid residues, and that proteins often are obtained from a natural source and can contain, for example, post-translational modifications. A polypeptide can be post-translationally modified by, for example, phosphorylation (phosphoproteins), glycosylation (glycoproteins, proteoglycans), which can be performed in a cell or in a reaction in vitro.

As used herein, the term "conjugated" refers stable attachment, typically by virtue of a chemical interaction, including ionic and/or covalent attachment. Among conjugation means are: streptavidin- or avidin- to biotin interaction; hydrophobic interaction; magnetic interaction (e.g., using functionalized magnetic beads, such as DYNABEADS, which are streptavidin-coated magnetic beads sold by Dynal, Inc. Great Neck, N.Y. and Oslo Norway); polar interactions, such as "wetting" associations between two polar surfaces or between oligo/polyethylene glycol; formation of a covalent bond, such as an amide bond, disulfide bond, thioether bond, or via crosslinking agents; and via an acid-labile or photocleavable linker.

As used herein, a composition refers to any mixture. It can be a solution, a suspension, liquid, powder, a paste, aqueous, non-aqueous or any combination thereof.

As used herein, a combination refers to any association between among two or more items. The combination can be two or more separate items, such as two compositions or two collections, can be a mixture thereof, such as a single mixture of the two or more items, or any variation thereof.

As used herein, fluid refers to any composition that can flow. Fluids thus encompass compositions that are in the form of semi-solids, pastes, solutions, aqueous mixtures, gels, lotions, creams and other such compositions.

As used herein, the term "solid support" means a non-gaseous, non-liquid material having a surface. Thus, a solid support can be a flat surface constructed, for example, of glass, silicon, metal, plastic or a composite; or can be in the form of a bead such as a silica gel, a controlled pore glass, a magnetic or cellulose bead; or can be a pin, including an array of pins suitable for combinatorial synthesis or analysis.

As used herein, a collection contains two, generally three, or more elements.

As used herein, an array refers to a collection of elements, such as cells and nucleic acid molecules, containing three or more members; arrays can be in solid phase or liquid phase. An addressable array or collection is one in which each member of the collection is identifiable typically by position on a solid phase support or by virtue of an identifiable or detectable label, such as by color, fluorescence, electronic signal (i.e. RF, microwave or other frequency that does not substantially alter the interaction of the molecules of interest), bar code or other symbology, chemical or other such label. Hence, in general the members of the array are immobilized to discrete identifiable loci on the surface of a solid phase or directly or indirectly linked to or otherwise associated with the identifiable label, such as affixed to a microsphere or other particulate support (herein referred to as beads) and suspended in solution or spread out on a surface. The collection can be in the liquid phase if other discrete identifiers, such as chemical, electronic, colored, fluorescent or other tags are included.

As used herein, a substrate (also referred to as a matrix support, a matrix, an insoluble support, a support or a solid support) refers to any solid or semisolid or insoluble support to which a molecule of interest, typically a biological molecule, organic molecule or biospecific ligand is linked or contacted. A substrate or support refers to any insoluble material or matrix that is used either directly or following suitable derivatization, as a solid support for chemical synthesis, assays and other such processes. Substrates contemplated herein include, for example, silicon substrates or siliconized substrates that are optionally derivatized on the surface intended for linkage of anti-ligands and ligands and other macromolecules. Other substrates are those on which cells adhere.

Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications.

Thus, a substrate, support or matrix refers to any solid or semisolid or insoluble support on which the molecule of interest, typically a biological molecule, macromolecule, organic molecule or biospecific ligand or cell is linked or contacted. Typically a matrix is a substrate material having a rigid or semi-rigid surface. In many embodiments, at least one surface of the substrate is substantially flat or is a well, although in some embodiments it can be desirable to physically separate synthesis regions for different polymers with, for example, wells, raised regions, etched trenches, or other such topology. Matrix materials include any materials that are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrlamide non-covalent composite, polystyrene-polyacrylamide covalent composite, polystyrene-PEG (polyethyleneglycol) composite, silicon, rubber, and other materials used as supports for solid phase syntheses, affinity separations and purifications, hybridization reactions, immunoassays and other such applications.

The substrate, support or matrix herein can be particulate or can be in the form of a continuous surface, such as a microtiter dish or well, a glass slide, a silicon chip, a nitrocellulose sheet, nylon mesh, or other such materials. When particulate, typically the particles have at least one dimension in the 5-10 mm range or smaller. Such particles, referred collectively herein as "beads", are often, but not necessarily, spherical. Such reference, however, does not constrain the geometry of the matrix, which can be any shape, including random shapes, needles, fibers, and elongated. Roughly spherical "beads", particularly microspheres that can be used in the liquid phase, are also contemplated. The "beads" can include additional components, such as magnetic or paramagnetic particles (see, e.g., Dyna beads (Dynal, Oslo, Norway)) for separation using magnets, as long as the additional components do not interfere with the methods and analyses herein. For the collections of cells, the substrate should be selected so that it is addressable (i.e., identifiable) and such that the cells are linked, absorbed, adsorbed or otherwise retained thereon.

As used herein, matrix or support particles refers to matrix materials that are in the form of discrete particles. The particles have any shape and dimensions, but typically have at least one dimension that is 100 mm or less, 50 mm or less, 10 mm or less, 1 mm or less, 100 µm or less, 50 µm or less and typically have a size that is 100 mm$^3$ or less, 50 mm$^3$ or less, 10 mm$^3$ or less, and 1 mm$^3$ or less, 100 µm$^3$ or less and can be order of cubic microns. Such particles are collectively called "beads."

As used herein, high density arrays refer to arrays that contain 384 or more, including 1536 or more or any multiple of 96 or other selected base, loci per support, which is typically about the size of a standard 96 well microtiter plate. Each such array is typically, although not necessarily, standardized to be the size of a 96 well microtiter plate. It is understood that other numbers of loci, such as 10, 100, 200, 300, 400, 500, 10$^n$, wherein n is any number from 0 and up to 10 or more. Ninety-six is merely an exemplary number. For addressable collections that are homogeneous (i.e. not affixed to a solid support), the numbers of members are generally greater. Such collections can be labeled chemically, electronically (such as with radio-frequency, microwave or other detectable electromagnetic frequency that does not substantially interfere with a selected assay or biological interaction).

As used herein, the attachment layer refers the surface of the chip device to which molecules are linked. A chip can be a silicon semiconductor device, which is coated on at least a portion of the surface to render it suitable for linking molecules and inert to any reactions to which the device is exposed. Molecules are linked either directly or indirectly to the surface, linkage can be effected by absorption or adsorption, through covalent bonds, ionic interactions or any other interaction. Where necessary the attachment layer is adapted, such as by derivatization for linking the molecules.

As used herein, a gene chip, also called a genome chip and a microarray, refers to high density oligonucleotide-based arrays. Such chips typically refer to arrays of oligonucleotides designed for monitoring an entire genome, but can be designed to monitor a subset thereof. Gene chips contain arrayed polynucleotide chains (oligonucleotides of DNA or RNA or nucleic acid analogs or combinations thereof) that are single-stranded, or at least partially or completely single-stranded prior to hybridization. The oligonucleotides are designed to specifically and generally uniquely hybridize to particular polynucleotides in a population, whereby by virtue of formation of a hybrid the presence of a polynucleotide in a population can be identified. Gene chips are commercially available or can be prepared. Exemplary microarrays include the Affymetrix GeneChip® arrays. Such arrays are typically fabricated by high speed robotics on glass, nylon or other suitable substrate, and include a plurality of probes (oligonucleotides) of known identity defined by their address in (or on) the array (an addressable locus). The oligonucleotides are used to determine complementary binding and to thereby provide parallel gene expression and gene discovery in a sample containing target nucleic acid molecules. Thus, as used herein, a gene chip refers to an addressable array, typically a two-dimensional array, that includes plurality of oligonucleotides associated with addressable loci "addresses", such as on a surface of a microtiter plate or other solid support.

As used herein, a plurality of genes includes at least two, five, 10, 25, 50, 100, 250, 500, 1000, 2,500, 5,000, 10,000, 100,000, 1,000,000 or more genes. A plurality of genes can include complete or partial genomes of an organism or even a plurality thereof. Selecting the organism type determines the genome from among which the gene regulatory regions are selected. Exemplary organisms for gene screening include animals, such as mammals, including human and rodent, such as mouse, insects, yeast, bacteria, parasites, and plants.

As used herein, the term "target site" refers to a specific locus on a solid support upon which material, such as matrix material, matrix material with sample, and sample, can be deposited and retained. A solid support contains one or more target sites, which can be arranged randomly or in ordered array or other pattern. When used for mass spectrometric analyses, such as MALDI analyses, a target site or the resulting site with deposited material, can be equal to or less than the size of the laser spot that is focussed on the substrate to effect desorption. Thus, a target site can be, for example, a well or pit, a pin or bead, or a physical barrier that is positioned on a surface of the solid support, or combinations thereof such as, but are not limited to, beads on a chip and chips in wells. A target site can be physically placed onto the support, can be etched on a surface of the support, can be a "tower" that remains following etching around a locus, or can be defined by physico-chemical parameters such as relative hydrophilicity, hydrophobicity, or any other surface chemistry that retains a liquid therein or thereon. A solid support can have a single target site, or can contain a number of target sites, which can be the same or different, and where the solid support contains more than one target site, the target sites can be arranged in any pattern, including, for example, an array, in which the location of each target site is defined.

As used herein, the term "liquid dispensing system" means a device that can transfer a predetermined amount of liquid to a target site. The amount of liquid dispensed and the rate at which the liquid dispensing system dispenses the liquid to a target site.

As used herein, the term "liquid" is used broadly to mean a non-solid, non-gaseous material, which can be homogeneous or heterogeneous, and can contain one or more solid or gaseous materials dissolved or suspended therein.

As used herein, the term "reaction mixture" refers to any solution in which a chemical, physical or biological change is effected. In general, a change to a molecule is effected, although changes to cells also are contemplated. A reaction mixture can contain a solvent, which provides, in part, appropriate conditions for the change to be effected, and a substrate, upon which the change is effected. A reaction mixture also can contain various reagents, including buffers, salts, and metal cofactors, and can contain reagents specific to a reaction, for example, enzymes, nucleoside triphosphates and amino acids. For convenience, reference is made herein generally to a "component" of a reaction, wherein the component can be a cell or molecule present in a reaction mixture, including, for example, a biopolymer or a product thereof.

As used herein, submicroliter volume, refers to a volume conveniently measured in nanoliters or smaller and encompasses, for example, about 500 nanoliters or less, or 50 nanoliters or less or 10 nanoliters or less, or can be measured in picoliters, for example, about 500 picoliters or less or about 50 picoliters or less. For convenience of discussion, the term "submicroliter" is used herein to refer to a reaction volume less than about one microliter, although it is apparent to those in the art that the systems and methods disclosed herein are applicable to subnanoliter reaction volumes, such as picovolumes, as well.

As used herein, nanoliter volumes generally refer to volumes between about 1 nanoliter up to less than about 100, generally about 50 or 10 nanoliters.

As used herein, with respect to the supports, an element is defined as less hydrophobic than another by the relative "wettability" of the element or contact angles, where the contact angle of an element is less than the surrounding surface. The contact angle is the angle that breaks the surface tension when a liquid is delivered. A hydrophilic substrate requires a relatively lower contact angle than a more hydrophobic material. Hence contact angle refers to relative hydrophobicity between or among surfaces. Hence loci on supports can be defined by their relative hydrophobicity/hydrophilicity to surrounding areas.

As used herein, high-throughput screening (HTS) refers to processes that test a large number of samples, such as samples of test proteins or cells containing nucleic acids encoding the proteins of interest to identify structures of interest or to identify test compounds that interact with the variant proteins or cells containing them. HTS operations are amenable to automation and are typically computerized to handle sample preparation, assay procedures and the subsequent processing of large volumes of data.

As used herein, symbology refers to a code, such as a bar code or other symbol, that is engraved, stamped or imprinted on a substrate. The symbology is any code known or designed by the user. In general, the symbols are identifiable to the user or are associated with information stored in a computer or memory and associated with identifying information.

As used herein, phenotype refers to the physical or other manifestation of a genotype (a sequence of a gene).

As used herein, the abbreviations for amino acids and protective groups and other abbreviations are in accord with their common usage and, if appropriate, the IUPAC-IUB Commission on Biochemical Nomenclature (see, (1972) *Biochem.* 11: 942-944).

As used herein, the amino acids, which occur in the various amino acid sequences appearing herein, are identified according to their known, three-letter or one-letter abbreviations. The nucleotides, which occur in the various nucleic acid fragments, are designated with the standard single-letter designations used routinely in the art.

It should be noted that any amino acid residue sequences represented herein by formulae have a left to right orientation in the conventional direction of amino-terminus to carboxyl-terminus. In addition, the phrase "amino acid residue" includes the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

As used herein, amplifying refers to means for increasing the amount of a biopolymer, especially nucleic acids. Based on the 5' and 3' primers that are chosen, amplification also serves to restrict and define the region of the genome that is subject to analysis. Amplification can be by any means known to those skilled in the art, including use of the polymerase chain reaction (PCR) and other amplification protocols, such as ligase chain reaction, RNA replication, such as the autocatalytic replication catalyzed by, for example, Qβ replicase. Amplification is done quantitatively when the frequency of a polymorphism is determined.

B. Systems and Methods

Systems that contain a data acquisition instrument, such as a mass spectrometer, an NMR instrument, a gas chromatograph, combinations thereof and other such instruments, that acquires data from a sample, such as a biological sample, and processors for assay-based judging decisions are provided. The processor contains programs (routines) for data collection and data analysis that are integrated, such as by a computer-based calling component, so that the instrument can provide real time (RT) diagnostic or other data typing results from samples tested. The data collection routines control the instrument for data collection; and the data analysis process controls the data collection process, for example, to determine a need for further sampling. The results from the data analysis are fed back (integrated) to the instrument and control thereof to assess the need for more sampling or testing.

Commercial MALDI mass spectrometers typically perform automated measurements on a series of samples. Software packages for automation include integrated algorithms that are used to judge the quality of the spectra. Such algorithms assess parameters such as the signal-to-noise ratio, peak resolution, and/or signal intensity within a specified mass range. If an acquired spectrum is determined to be of low quality, the instrument parameters can be adjusted and/or the stage can be moved ("rastered") to another section of the sample for re-acquisition of the spectrum. The cycle of evaluation and re-acquisition is repeated until either a spectrum of sufficient quality is acquired or a pre-specified number of acquisition attempts have been made. The spectrum is then saved and the system moves on to the next sample.

In these systems, the integrated judging algorithms make determinations based on qualities of the spectra that are independent of the underlying assay or biological information contained in the spectra. During an automated run, a spectrum for each sample is stored. Then special purpose algorithms are employed that automatically determine the sample genotype. For example, the SPECTROTYPER mass spectrometry system (Sequenom, Inc., San Diego, Calif.; see, also U.S. application Ser. No. 09/285,481 filed Apr. 5, 1999, published as U.S. application Publication No. US-2002-0009394-A1; International PCT application No. WO 02/25567) is an automated data processing system that among other determinations, determines one or more genotypes in each sample depending on the assay definition for that sample and assigns each a quality, generally from best to worst and/or conservative, moderate, aggressive, low probability or bad spectrum.

In the above-described systems, a combination of automated data collection routines and automated data processing routines, two different sets of criteria are used to judge the spectra; one set of criteria is used to control the data acquisition process and a separate set is used to determine the biological significance of the acquired spectrum. Using such two-step acquisition and analysis routines, however, can result in missed calls and unnecessarily long acquisition times. This is because the spectral features that define a "clean" acquisition are not necessarily the same features required for, for example, accurate genotyping. For example, the presence of large primer peaks due to incomplete extension can render a spectrum acceptable in terms of signal to noise criteria in a predefined mass window, but the resulting spectrum might not be of sufficient quality to allow determination of an unambiguous genotype. It is also possible that a spectrum that is of high quality for genotyping has a signal-to-noise ratio that causes repeated sampling by the data collection algorithm. In this case, unneeded data are collected with a corresponding decrease in throughput. When different criteria are used for data collection and for data analysis it is always possible that either the data collected do not give a suitable biological result or that extra data are collected resulting in lower throughput. Furthermore, the mismatches between the two judging methods become more common as the spectra from a sample become more complex, as with highly multiplexed samples.

The methods and systems herein provide integration of the algorithms for data analysis and data collection and result in faster, more accurate MALDI analyses, such as genotyping. An exemplary system provided herein, which is a modification of systems, such as the SpectroTyper™ system, includes highly optimized versions of the calling algorithms with a streamlined interface to a database to store the results of analyses, such as genotyping results. As part of the optimization, a well defined programming interface that controls the dialogue between the data acquisition component and the biological-calling component of spectra analysis is provided. The interface is flexible and modular to allow modification of the calling algorithms.

With the systems and method provided herein, the biological results, such as a genotype, guide data acquisition decisions, not instrument output such as a mass spectrum. The systems herein consider the ultimate biological results, not the output of the instrument, and determines whether the results are good enough. The system directs the instrument to obtain further data. In some embodiments, the system can eliminate further processing steps in a particular assay if it repeatedly fails. The results of the assays, not necessarily the instrument's results, are displayed, and can be displayed in real-time.

The instruments as provided herein display, not (or not only) the direct instrument output, such as a mass spectrum or spectra, the desired result, including a diagnosis, such as a genotypes or allelic frequency. Hence, for example, a mass spectrometer that includes a display biological result of a diagnostic test, such as the genotype or diagnosis or allelic frequency, is provided.

The methods and systems provided herein permit multiplex analyses including analyses of multiple reactions in a sample, and multiple sample analyses. They also permit real time analysis and output of diagnostic tests that require analysis and identification of a plurality of markers. The processes herein permit the each assay to be considered and can assess each assay in a multiplexed reaction and determine the results from each assay. For example, there are about twenty markers associated with cystic fibrosis (CF). For a clinical test for CF that analyzes all twenty markers, it may not be possible to perform all twenty in one multiplex reaction. Multiple samples could be required. The methods and systems provided herein permit this to be done and the results from different samples combined if needed. Using the algorithms, systems and methods provided herein, results from several samples are obtained as are the results over multiple samples. Hence the methods and systems provided herein connect a plurality of related measurements, such as measurements that have related biological meaning. The ultimate output is a diagnosis, such as a genotype, which can be derived from the results of tests of a plurality of samples. For the output, it does not matter whether there is one mass spectrum or a plurality thereof.

A potential problem with a system that runs biology based signal processing in real-time is throughput. The biology based algorithms can take a significant amount of time to run. The hardware and software provided herein solve these problems and permit biology-based instrument control and high throughput analyses.

The assay based judging and machine control described herein has been used to run many high density arrays, such as 384 and 96 position chips, using a wide range of assays and nucleic acid-containing samples and can be used for higher density formats, such as but are not limited to, 1534 and higher. The improvement in calling efficiency has been observed to range from 0% to over 50%. The degree of improvement depends on the quality of the assay and the level of multiplexing For example, a typical experiment involved forty-eight assay, four-plex tests that were performed on eight different DNA groups (384 reactions) and were deposited on a 384-spot chip (see, EXAMPLES, FIG. 9 and FIG. 10). The same chip was measured consecutively on three mass spectrometer instruments. The first run was performed without the data analysis application software. The "standard" configuration instrument uses fuzzy logic to control rastering based on resolution and signal-to-noise ratio over a fixed mass range. Thus, the biological result (e.g. genotype) is not used in controlling the instrument. The next two runs were performed using the data analysis biological-results control described above and as provided herein. The data results are presented below in EXAMPLE 3 (Table 1). It should be noted that the quality of data is expected to decrease from consecutive data runs, because the sample is depleted by successive laser shots, and thus call efficiency should decrease. The results in Table 1 (see EXAMPLE 3) show that the call efficiency was improved by using assay-based judging in accord with the methods and systems provided herein to control data acquisition. In particular, overall call efficiency was improved from 77% for the "standard" configuration to 90.9% in the first data run using the assay-based judging.

As exemplified, the assay-based judging provided herein added shots from different raster positions until all assays provided acceptable results, up to the shot limit per sample. Thus, the assay-based judging is not misled by large primer peaks in the spectrum output or by large peaks that come from assays other than the assay of interest. In the spectral output, for example, the peaks at mass 6261 and at mass 6574 can be compared between FIG. 9 and FIG. 10 (see, EXAMPLE 3). It is known that these peaks represent the C and A alleles of one of the assays in the sample. From the FIG. 10 spectrum, it is clear that the assay should be called CA, and the system using the assay-based judging provided herein made a CA call with a conservative score. Viewing the FIG. 9 spectrum, it is less clear what the call should be. It can be seen that the peak at mass 6261 is especially noisy. In such a case, averaging in more shots from a different section of the sample would help, but the "standard" configuration judging is misled by good signal-to-noise peaks in the spectrum so that the spectrum is judged sufficient and the system proceeds to the next sample without acquiring additional data. The benefits of assay-based judging and data processing as provided herein are advantageously realized in multiplexed assays.

C. Description of Exemplary Embodiments

1. Testing System

Referring now to FIG. 1, a diagrammatic representation of an exemplary testing system 10 for testing a biological sample. Generally, the testing system 10 contains a real time (RT) workstation 12, which includes a series of controllers that retrieve assay design parameters from a database maintained by a database server 13 and directs the acquisition and processing of data indicative of the biological sample from a mass spectrometer 14. The processed data or genotyping results are then downloaded into a directory at the database server 13.

With the testing system 10 generally disclosed, exemplary individual components are as follows. The testing system 10 has a RT workstation 12 that can be, for example, a computer system having storage and computational components, including one or more controllers. In one embodiment, the RT workstation includes an assay controller 30 (also referred to as a plate editor) that acquires assay design specifications from the database server 13, includes a data acquisition controller 31 which automatically aligns the laser on a chip using an image system, controls the motor movement of the assay substrate at the mass spectrometer, and acquires the data signal directly from the mass spectrometer, and also includes a real-time data analysis controller 32 that communicates with the controller 31 by receiving a data signal and providing instruction for additional data acquisition. Additional data acquisition can be dependent on the quality of the data previously obtained. As described further below, the data quality can be assessed with respect to assay results, such as whether a determination about the spectra results can be made. The data can be stored on a local hard drive of the RT workstation 12 until the results from all the samples are compiled. The compiled data is stored in a directory in the database server 13. The RT workstation 12 can include a display 16 for visually communicating test results and status information.

In one embodiment, the RT workstation 12 is a computer, such as an IBM-compatible Personal Computer system, communicating with the mass spectrometer using a known communication standard, such as a parallel or serial interface. It can be appreciated that the workstation and controllers can be alternatively embodied. For example, the RT workstation 12 can be integral to the mass spectrometer 14 or another system component, or the workstation 12 and controllers 30, 31, 32 can be placed at a remote location from the mass spectrometer. In such a manner the network topography, such as a wide area network or a local area network, would provide a communication path between the mass spectrometer 14 and the RT workstation 12. Although the RT workstation 12 can be standalone computer device, it can be appreciated that one or more of the controllers 30, 31, 32 can be, for example, a microprocessor or other programmable circuit device capable of performing a programmed process. Moreover, it can be appreciated that the workstation 12, one or more of the controllers 30, 31, 32, and the database server 13 can be integrated into a single device, or can be separate, independently operating devices.

The mass spectrometer 14 can be a MALDI Time-of-Flight (TOF) instrument, which are known to those of skill in the art (see, e.g., such a co-pending U.S. patent application Ser. No. 09/663,968 filed Sep. 19, 2000 and entitled "SNP Detection Method", and U.S. patent application Ser. No. 09/285,481 filed Apr. 5, 1999 and entitled "Automated Process Line", and published as U.S. application Publication No. US-2002-0009394-A1). The mass spectrometer 14 is configured with an interface to communicate with the workstation controller 12. The interface can be designed to conform to a known data communication standard, for ease of connection. Although a single interface can enable the controller 12 to both receive data from the mass spectrometer 14 and send instructions to the mass spectrometer 14, two or more separate interfaces can be used. Although the exemplary test system 10 incorporates a MALDI TOF mass spectrometer, it can be appreciated that other types of analytical instruments and mass spectrometers can be used.

The testing system 10 can provide the database server 13 with one or more databases, such as database 18, database 19, database 20, database 21 and database 22 stored in direct access storage devices. Such databases can store assay design, genotype profiles, allelotype profiles, mass spectra and other such data or instruction sets. It can be appreciated that other forms of data storage can be used. A structured database provides a convenient format for storing and retrieving data. In an exemplary embodiment, one of the databases, such as database 18, stores assay design information, a database 19 stores genotyping profiles, a database 20 stores allelotyping profiles, database 21 stores sample identification information, while the other database 22 stores test results for later analysis. It can be appreciated that fewer or more databases can be used to store assay and test information. If desired, the databases can be distributed between the workstation 12 and the database server 13. The database server 13 can also contain one or more controllers such as controller 23 and controller 24. In an exemplary embodiment, the controller 23 monitors the data acquisition of the individual samples on the assay substrate or chip. Once the data are received from all samples in the assay, the data monitoring controller 23 downloads all or part of the assay information and stores the information in a directory in the test results database 22. The controller 24 imports the data into a directory in the results database 22.

The RT workstation 12 has sufficient processing ability to extract assay design information from the assay design database 18, and to convert the assay design information into a format for providing specific directions to the mass spectrometer 14. For example, the controller can access the database 18 and request a specific assay design. The specific assay can be set up to provide a microtiter plate with hundreds, or even thousands, of samples on each plate. The test can require that samples be tested in a specific order, and based upon the result from previous tests, the order can be adjusted, or some samples can even be eliminated from the assay. The RT workstation receives the assay design information and converts the assay design information into commands for the mass spectrometer 14. Upon starting the assay, the RT workstation 12 sends initialization commands to the mass spectrometer 14 consistent with the assay design.

Extracting an assay design from a database and generating mass spectrometer commands can be a time consuming and processor intensive operation. It would be particularly undesirable for the extraction process to interfere with the more real-time control of the mass spectrometer. Accordingly, the RT workstation 12 can be designed to perform a database extraction process, and database storage functions, as background tasks, or at a time when such tasks do not interfere materially with the more real-time control of the mass spectrometer 14.

The RT workstation 12 defines a physical map of the biological samples on the assay plate or chip by manual input of information by the operator or an automated scanning system such as an optical reader or other such reader to read bar codes or other symbologies, where a symbology, such as bar code information, identifies the plate or chip.

A mass spectrometer 14 receives the biological sample for analysis and generates an electrical data signal representative of information, such as a genotype, associated with the sample tested under direction from the real time workstation 12. The instrument is initialized when it is provided with specific data acquisition parameters, either manually or in a default mode. The acquisition parameters can include the number of laser shots per spot, the maximum number of raster iterations per sample, and voltage, delay time, calibration constants and other parameters that are well-known to those skilled in the art. The mass spectrometer is initialized according to test assay parameters, and acquires data indicative of the biological samples. More particularly, the data acquired by the mass spectrometer is typically in the form of an electronic data spectrum. The electronic data spectrum can be retrieved by the RT workstation.

Biological samples are analyzed when the RT workstation 12 directs the automatic alignment of the mass spectrometer laser onto an assay surface or chip using an imaging system and controls movement of the laser from sample to sample, and from assay surface to assay surface when multiple assay surfaces or chips are held in a multi-component support.

Biological information, such as genotyping information, is acquired directly from the mass spectrometer 14 by the RT workstation 12. The signal is converted into a mass data spectrum by the RT workstation 12 where a genotype is determined. If the sample information, such as the genotype, cannot be called, the RT workstation 12 recognizes the situation and directs an adjustment to the mass spectrometer 14. For example, if the acquired spectrum has an unacceptably low signal to noise ratio, the workstation controller 12 can direct the mass spectrometer 14 to test the same sample again, but can adjust the mass spectrometer 14 to direct its beam at a different spot on the sample, or can select alternative power settings or measurement filters. In another example, the controller 12 can direct the mass spectrometer 14 to take a series of data sets from the same sample until the standard deviation in the aggregate results achieves a desired degree of certainty.

It should be understood that, even though the same sample can be tested multiple times, each test is taken from a unique spot on the sample.

As noted, in accord with the methods and systems provided herein, the test criteria additionally involve the results of the assays performed. A system provided herein uses biology-based decision outcomes (such as conclusions about genotype of a sample) to control the operation of the test machine and to determine if repeated testing (mastering) is needed.

The modular design of an exemplary embodiment, with a data acquisition component and data analysis component (FIG. 1), provides a great deal of flexibility. Each component can be modified in operation to develop special purpose operation and control for calling biological assays. Thus, the component operation can be modified to suit different assay types. Those skilled in the art understand that a wide variety of component interface configurations can be used to facilitate communications between the analysis software application components.

2. RT Workstation

Figure 7:
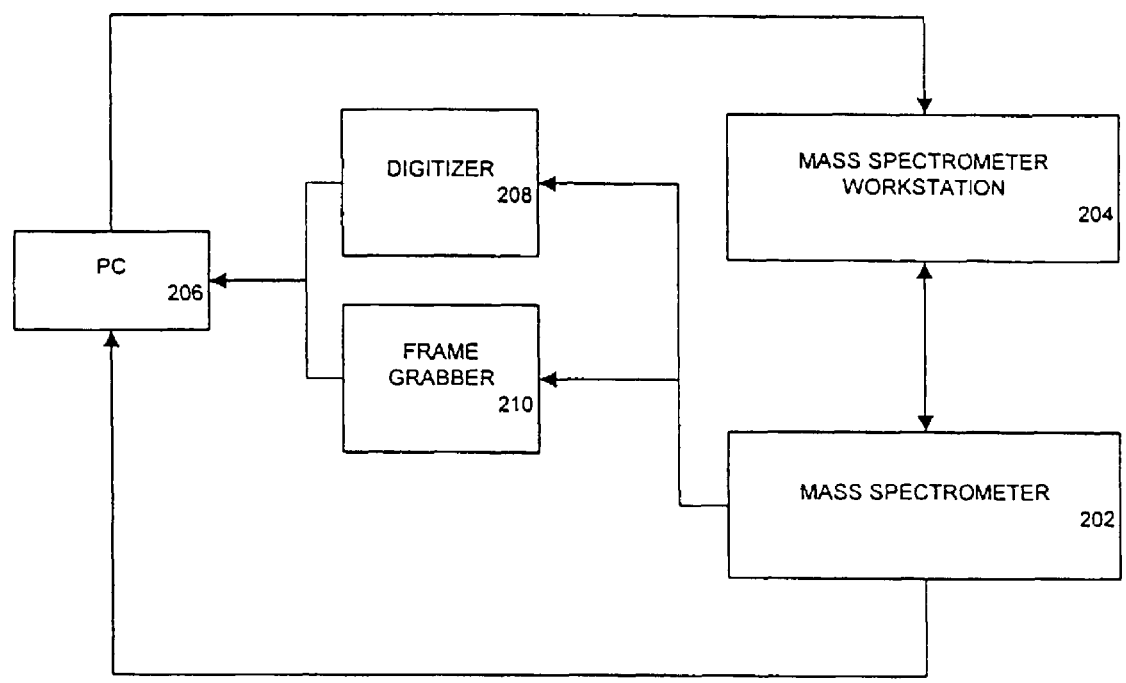
FIG. 7 is a block diagram of an exemplary testing system provided herein, in which the instrument is a mass spectrometer (it is understood that the mass spectrometer is exemplary only and can be replaced by any such data acquisition instrument).

FIG. 7 depicts the RT workstation of FIG. 1. Components 206, 208, and 210 are part of the RT workstation 12 in FIG. 1; components 204 and 202 make up the mass spectrometer 14 in FIG. 1. FIG. 7 is a block diagram of an exemplary testing system 200 provided herein. The system of FIG. 1 using the RT station of FIG. 7 and processing in accordance with FIGS. 2 and 4, discussed below, provides efficient instrument operation. In the embodiment of the RT station depicted in FIG. 7, a mass spectrometer instrument 202 that is controlled by a mass spectrometer workstation 204 communicates with a computer analysis workstation 206 that operates in accordance with the description herein. Exemplary instruments, include a MALDI time-of-flight instrument, such as a "Biflex" mass spectrometer available from Bruker Daltonik GmbH of Bremen, Germany. The instrument controlling workstation 204 can include, for example, a Sun workstation, available from Sun Microsystems, Inc. of Santa Clara, Calif., USA.

The workstation 206 can be configured as a Personal Computer (PC) equipped with a digitizer 208 and a frame grabber 210. The frame grabber receives video image data from a sample visualization camera (not illustrated) of the instrument that is part of the machine visualization system described above. The frame grabber can include the model IMAQ PXI-1411 from National Instruments Corporation of Austin, Tex., USA. The digitizer 208 receives analog data and converts it to a digital representation. The digitizer can include, for example, a model "PDA500" 500-MHz, 8-bit digitizer from Signatec, Inc. of Corona, Calif., USA.

Figure 6:
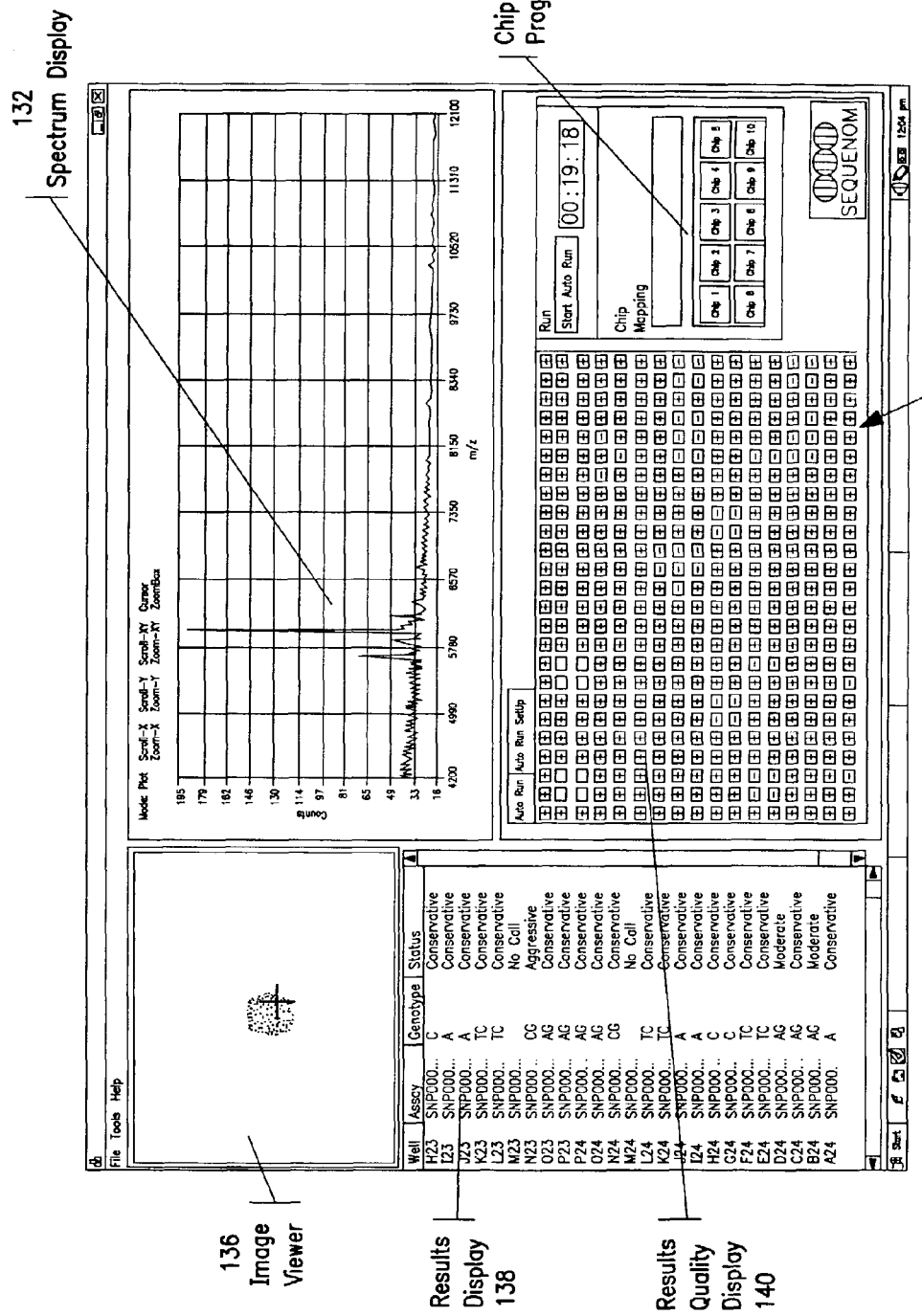
FIG. 6 is an illustration of a computer display showing results from a testing system.

In the system 200, four signals that ordinarily are routed between the instrument 202 and the instrument workstation 204 are instead routed between the instrument and the computer analysis workstation 206. The four signals are included in or form the output of the MCP detector of the instrument, the trigger control for the laser and high voltage electronics of the instrument, the output of a photodiode detector used to trigger data acquisition, and the video signal from the sample visualization camera. The video signal provides the image viewer display 136 (FIG. 6). The output of the MCP detector passes through a gain-five amplifier and a passive low-pass filter having a cutoff frequency of 90 MHz. The amplifier can include, for example, a Stanford Research Systems SR445 amplifier (Stanford Research Systems, Inc. of Sunnyvale, Calif., USA), and the low-pass filter can include, for example, a Mini Circuits BLP-90 filter (Mini-Circuits, Inc. of Brooklyn, N.Y., USA).

The instrument workstation 204 and the computer analysis workstation 206, for example, can communicate with each other using a network connection protocol, such as the TCP/IP protocol. The communications are used by the computer analysis workstation 206 to move the sample handling stage of the instrument 202 from sample to sample of a plate or chip, and to move the stage so as to position each individual sample beneath the laser of the instrument to different raster positions.

Thus, the computer analysis workstation 206 has the capability of acquiring spectra output, processing the output, and controlling the instrument 202 according to the output in real time. The instrument output in terms of biology based results, such as genotype, are used to determine if a sample should be rastered (multiple data acquisition from the same sample). The workstation 206 executes a software application from which a user can specify a number of setup operating parameters to control decision making. The software application is installed at the workstation 206 into program memory (not illustrated). The installation can occur, for example, through magnetic media (floppy disks) or optical media (such as CD discs or DVD data discs) or can occur through network communications download. This permits the operation of the workstation to be easily modified through modifications to the application software.

For example, in an exemplary embodiment, the analysis workstation 206 is setup to run a series of samples through the instrument wherein, for each sample, a predetermined, set number of instrument activations (laser shots) are performed and output is averaged to create the spectra produced by the instrument. The number of shots per sample can be specified by a user for a sample run. The workstation collects the shot results, averages them, and then independently judges each assay that was defined or specified for that sample. If the result of judging (the assay score) for a sample is less than a "moderate" ranking, then the workstation 206 causes additional data collection (mastering) from the instrument for the assay in question.

Any additional data from a sample that is ordered by the workstation 206 is averaged together and the data are added to the first data collected from the instrument 202. The result for the assay is determined, as before, and if the assay score is improved by the addition of the new data, then the new summed data collection is kept. The cycle of data collection and judging continues until a set number of shots or attempts has exceeded a predetermined limit number, or until a score achieving a "moderate" ranking or better is achieved for each assay in a sample. The operation of the system 200 is described in greater detail with respect to FIG. 4.

3. Exemplary Testing Processes

Figure 2:
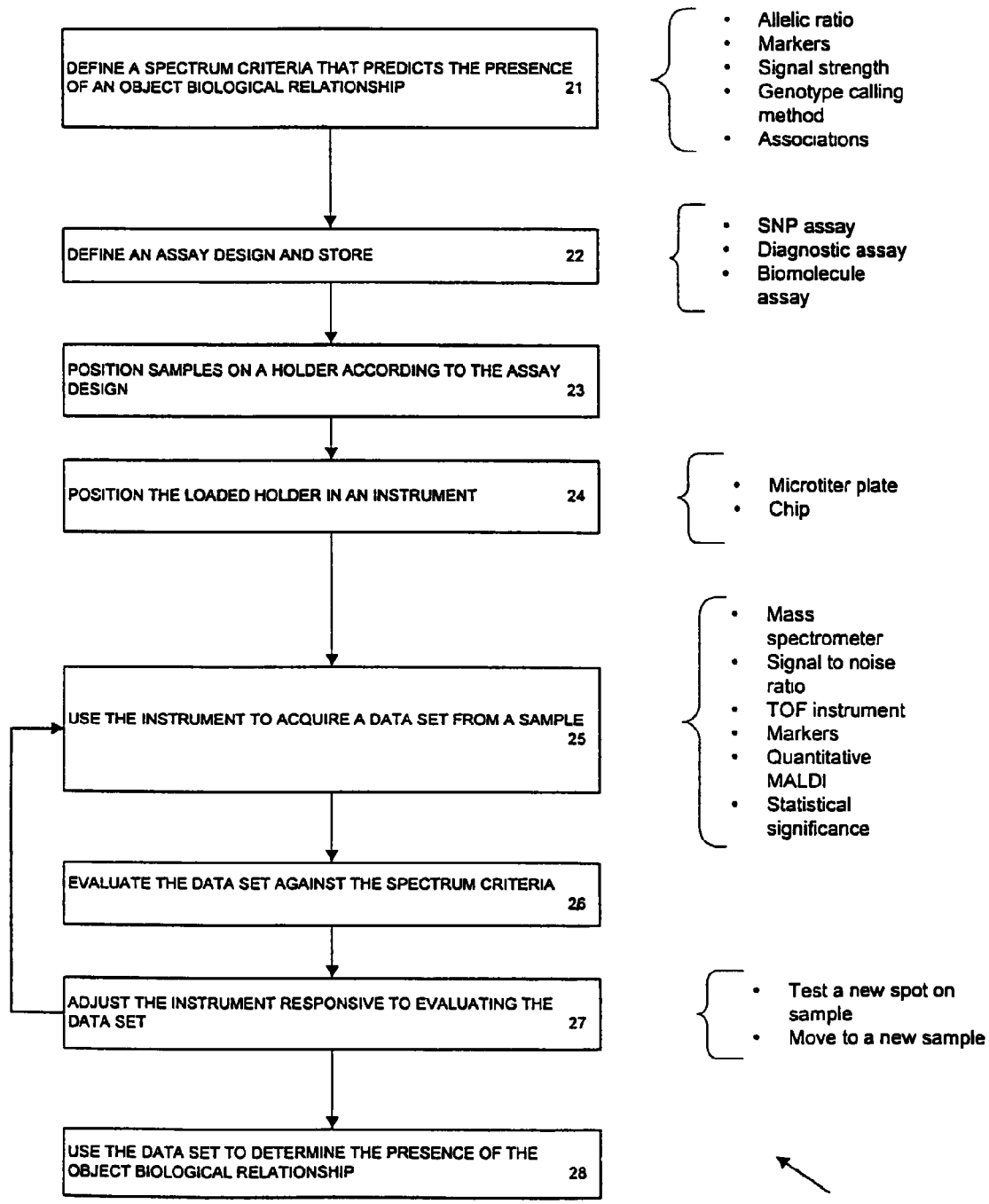
FIG. 2 is a flowchart of a testing process provided herein.

Referring now to FIG. 2, a method of testing a biological sample is shown. The exemplified method of testing first predefines spectrum criteria that predict the presence of a biological relationship in block 21. Such criteria include, but are not limited to, allelic ratios, markers, signal strength, genotype calling method and associations. The predefined spectrum criteria vary depending on the assay to be run. For example, the spectrum criteria can be set to assure a minimum allelic ratio is exceeded. In this regard, the spectrum criteria can be set to reject acquired data where the allelic ratio is below a threshold, such as 5%. In another example, the presence of specific markers can be required to validate acquired data. In another example, the spectrum criteria can require that a peak exceed a signal to noise figure before accepting the acquired data as valid. Further, statistical methods can be applied to the acquired data, or sets of acquired data, to determine if a particular peak is statistically significant. Using such a statistical method can dramatically increase the accuracy of calling the composition of a biological sample (see, e.g., co-pending U.S. patent application Ser. No. 09/663,968 filed Sep. 19, 2000 and entitled "SNP Detection Method", and U.S. patent application Ser. No. 09/285,481 filed Apr. 5, 1999 and entitled "Automated Process Line", and published as U.S. application Publication No. US-2002-0009394-A1, which exemplify application of statistical methods acquired spectrum data). It can be appreciated that the spectrum criteria can be defined in numerous ways consistent with the teachings herein.

With the spectrum criteria predefined, block 22 shows that the assay design is defined, and then can be stored in a database for use in controlling the instrument. Exemplary assays include, but are not limited to, SNP detection/identification assays, diagnostic assays, biomolecule detection/identification assays and other assays, particularly assays that involve detection and/or identification of a biomolecule or biopolymer. In an exemplary embodiment, the instrument is a MALDI TOF mass spectrometer. It can be appreciated that other instruments, including other mass spectrometers, can be substituted. The defined assay design is used to generate the initial settings for the instrument, and then is further used to direct the instrument during the assay test.

Biological samples are then positioned in block 23 for test in the instrument as defined and required by the steps and protocol of a particular assay. The samples can be positioned on a support (holder), such as a microtiter plate. It can be appreciated that other types of supports, including but are not limited to test tubes or chips, can be substituted for a microtiter plate. Although it is more convenient to place all samples for one assay on a single support, samples for a single assay can be placed on multiple supports.

The support is positioned in the instrument, as indicated in block 24. The support can be manually positioned, or can be positioned under robotic control. If the support is robotically controlled, then information extracted from the assay design can be used to direct the robotic control to place the proper support in the instrument. If manually positioned, a visual display can be used to assist the human operator in identifying and verifying the proper support.

Blocks 25-28 represent the real time control of the instrument and are described further below. This real time control permits the automated and efficient operation of the instrument, and provides accuracies and repeatabilities in test results that are not available in known systems.

In block 25, the instrument acquires a data set from a biological sample. In an exemplary embodiment, the acquired data are in the form of an acquired data spectrum. In the exemplary system described in the '968 application referenced above, the data set is generated by first finding the height of each peak, then extrapolating a noise profile, and finding noise of each peak, next calculating signal to noise ratio (s/n ratio), and finding residual error, and calculating and adjusting signal to noise ratio, and developing a probability profile, and determining peak probabilities, and determining allelic penalty, and adjusting peak probability by allelic penalty, and calculating genotype probabilities, and testing ratio of genotype probabilities.

The acquired data are evaluated in block 26. In an exemplary embodiment, the acquired data are compared against the spectrum criteria previously defined. As described above, this comparison can be, for example, a comparison of peak strength, peak position, markers, s/n ratio, allelic ratio, or a statistical calculation. Further, the comparison can be multi-dimensional, for example, requiring first that a particular marker be located and then testing that an appropriate signal to noise ratio exists. It can be appreciated that the comparison step 26 can use data from multiple acquired data sets, for example, to calculate the standard deviation for the group. Accordingly, the comparison compares the standard deviation in the group of data sets to determine if the results should be derived from the newly acquired data.

Responsive to the comparison, the workstation controller adjusts the instrument in block 27. For example, if the signal to noise ratio was too low in a first data set, the instrument can be adjusted to test the same sample, but at a different spot on the sample. By moving to a new target spot, new data can be acquired for the same sample. This is referred to as rastering. In testing the new spot, it is quite possible that different or better analytical results can be found. Thus, taking a reading at a second spot can enable making an analytical call on a sample when it was not possible with only a single spot test. Further, testing additional spots on an individual sample can permit the calculation of aggregate results with a lower error rate than relying solely on a single test spot. By automating the evaluation of the acquired data and control of the instrument, the overall assay test can be manipulated to provide a requisite level of accuracy and tolerance. Accordingly, the maximum number of samples can be accurately called for a particular assay, but yet time and system resources are not wasted by testing more spots than necessary.

In particular, using assay results or outcome as a test criteria to control further sample testing has been found to increase the efficiency and throughput of the testing system by reducing unnecessary test cycles (mastering) and increasing the reliability of the test results.

After the instrument is adjusted and set to acquire a next data set, the method returns to block 25 to acquire the next data set. As described above, the next data set can be for the same sample, or the instrument can have been adjusted to the next sample. After testing is completed, processing moves to block 28.

Block 28 shows that the results from the acquired data are analyzed to determine the presence of an object biological relationship. For example, the assay can be attempting to locate particular single nucleotide polymorphisms (SNPs), or can be allele typing, or can be genotyping. Irrespective of the particular biological relationship searched for, the relative success of the search can be used by the FIG. 2 testing method in directing further data acquisitions. For example, if in a multiple sample assay, the biological relationship is ruled out after only the first sample, then the method can be directed to skip testing the rest of the samples in the assay and move on. In another example, if after testing multiple samples for a particular assay the results are still ambiguous, block 28 can be used to determine if the ambiguity can be removed by increasing the certainty of the results for a particular sample. If so, the test can be directed by the workstation to automatically take additional data acquisitions and attempt to salvage the assay. Without such an automated and intelligent process, the assay would be rejected. Accordingly, the FIG. 2 testing method provides a higher level of calls, and a higher level of call certainty than with known testing methods.

Figure 3:
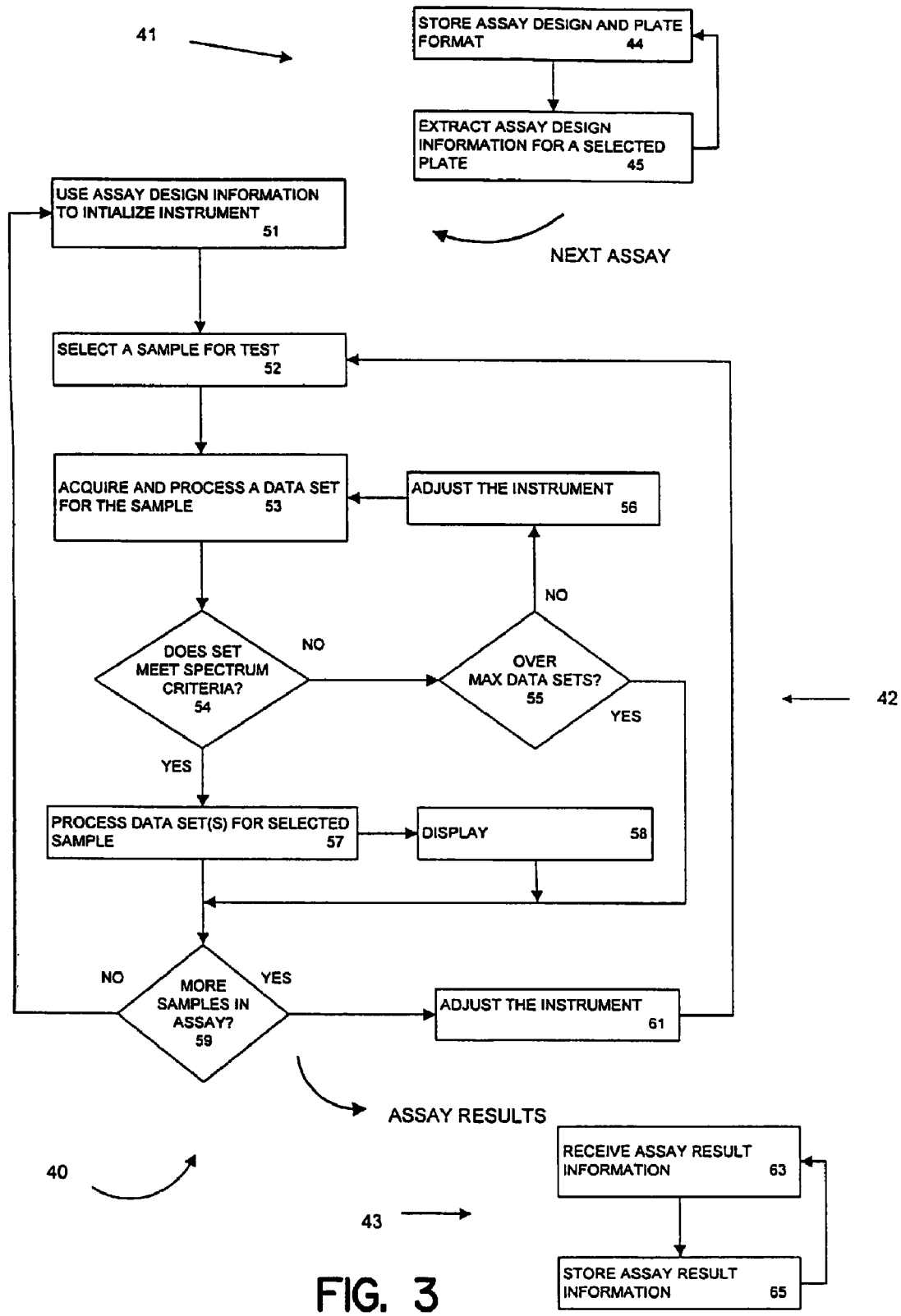
FIG. 3 is a flowchart of a testing process provided herein that illustrates automated control of a testing instrument.

Referring now to FIG. 3, another method of testing a biological sample is shown. The FIG. 3 testing method 40 generally has an initialization loop 41, a control loop 42, and a results loop 43. The control loop 42 is responsible for acquiring data sets, comparing the data sets to predefined spectrum criteria, and adjusting the instrument responsive to the evaluation of the acquired data. In this regard, the control loop must operate efficiently enough to permit the timely operation of the overall test system. Therefore, certain of the setup and storage functions have been off-loaded to the background loops 41 and 43. It can be appreciated that more or less functionality can be placed in the background loops 41, 43 to accommodate different response times needed in the control loop 42.

The initialization loop 41 is a background loop that permits storage of assay design and plate information in block 44. Typically, the assay design and plate information is stored in a database form. Typically, the database of assay design and plate information can be used by multiple test systems, and can be accessed remotely. In such a manner a remote researcher can define an assay in a single database, and that newly defined assay can be operated on multiple test systems.

Since extracting and converting the assay information into control information is a time consuming process, the extraction process is performed in block 45. Of course, it can be appreciated that as typical computer workstation computational powers increase, it can be desirable to have the extraction process made a part of the control loop 42. Since the extracting step is generally a background step, the extraction process can be performed for a next assay while the control loop 42 is actively performing an assay. Thus, when the control loop has finished an assay, the extracted information from block 45 can be sent to block 51 to start the control loop 42 for a next assay.

The information from block 45 is received in block 51, where the information is used to initialize the instrument. In an exemplary embodiment, the instrument is a MALDI TOF mass spectrometer. The initialization commands can include identifying the first sample to test, the proper power settings, and the desired filtering for the data.

A sample is selected for test in block 52, and data are acquired from the test sample in block 53. The acquired data can be sufficiently processed to determine target characteristics for the acquired data. For example, if signal to noise ratio is an important indication of test quality, then a signal to noise ratio can be calculated for the acquired data. More particularly, the acquired data are processed to facilitate comparison with predefined spectrum criteria.

The predefined spectrum criteria, as previously discussed, define the analytical characteristics for good data. In block 54, the acquired data are compared to the predefined spectrum criteria and is further processed in block 54 to extract biological information. If the acquired data are good, a "YES" outcome at block 54, and the data are formatted and displayed in block 58. If the acquired data are not good, however, a "NO" outcome at block 54, then block 55 asks if the maximum number of spots have been shot for this sample. Box 55 is check for the maximum number of rasters. For example, a typical mass spectrometer can take a maximum of about 15 to 20 shots on any given sample. To assure the integrity of the test, it can be advisable to set the maximum to a safe number, such as 20, or other number depending upon the sample and the instrument. The sample is not further processed if the maximum number of rasters has been exceeded (a "YES" outcome at block 55). At each raster position, 20 laser shots are measured and averaged to get a spectrum from that laser position. Thus, if less than 10 spots have been shot, a "NO" outcome at block 55, then the instrument is adjusted to a new spot in block 56, and data are acquired on the new spot in block 53. In block 54, the newly acquired data are compared to the spectrum criteria. Alternatively, block 54 can use aggregated data from multiple test spots to determine if the aggregated data are good.

Once a sample has been judged to provide good or bad assay results, or if the maximum shots have been exceeded, then block 59 asks if there are more samples in the assay. If so, a "YES" outcome at block 59, then the instrument is adjusted in block 61 to shoot the next sample. If all the samples have been tested, a "NO" outcome at block 59, then the control loop 42 resets and a next assay loop is initiated at block 51.

When the control loop 42 is complete, then the results from the assay are passed to the background results loop 43. The results loop 43 can perform additional post processing on the data in block 63, which can include a manual review of the results. The data and results can then be stored in block 65. Typically, the data and results are stored in a database that is accessible from remote locations so a remote researcher or other test operators can review the results. The loop repeats for all assay results.

Figure 4:
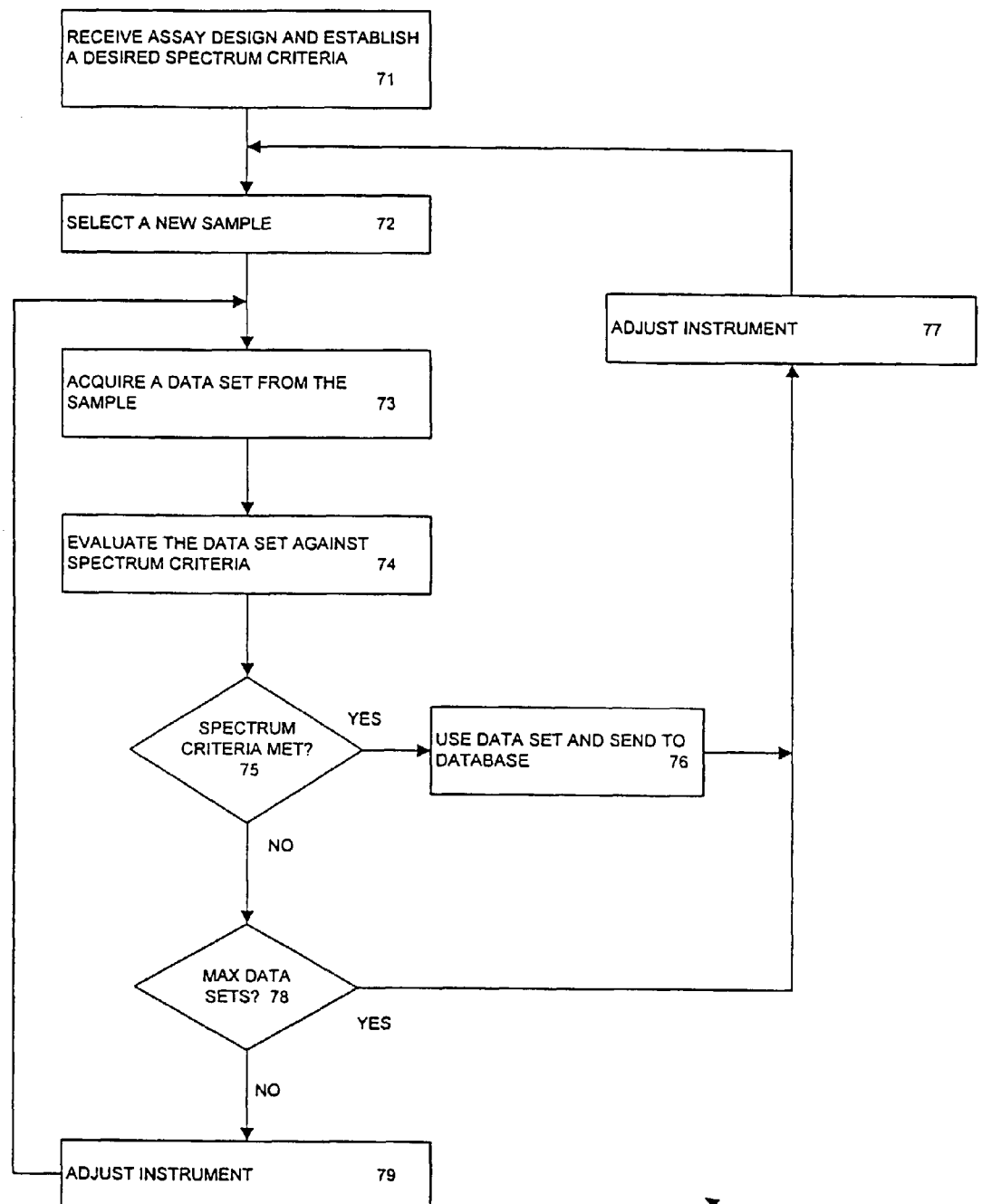
FIG. 4 is a flowchart of a testing process provided herein that illustrates an assay-based judging process provided herein.

Referring now to FIG. 4, another testing method 70 is illustrated. The testing method 70 allows an assay designer to establish a minimum standard for each biological sample in block 71. More particularly, the testing method 70 is directed to increasing the confidence in the results from each sample. As discussed above, a typical mass spectrometer can take a data set from multiple spots on a single biological sample. The testing method 70 enables the test to dramatically increase the confidence for each sample, while minimizing the number of testing samples that must be acquired.

In the testing method 70, a biological sample is selected in block 72, and a data set is acquired in block 73. In block 74, the acquired data are evaluated against the data criteria set for the sample. For example, the data criteria can expect a signal to noise ratio to exceed a floor value. In this regard, each data set acquired for a particular sample is compared against the data criteria. Alternatively, data collected from multiple shots in the same sample can be used in the comparison. For example, the data criteria can require that the standard deviation between spots on the same sample not exceed a particular value. Thus the comparison step could include determining the standard deviation for all spots in the single sample to determine if confidence is sufficiently high to call the sample. It can be appreciated that the comparison step can entail a wide range of analytical and algorithmic calculations, either on individual data sets or aggregates of data sets.

Importantly, the testing method 70 permits setting the data criteria in a manner that minimizes the number of data acquisitions. For example, the data criteria could be to accept a sample when a single data set has a signal to noise ratio meeting one level, or meeting a lower level for aggregate data sets. Thus, a single strong reading would be sufficiently robust, and multiple shots would not be needed on that sample. In a similar manner, the comparison could be set to accept sample data if the standard deviation between two successive shots is less than 5%, or accept the data if the standard deviation is less than 7% for 3 shots, or less than 10% for 4 or more shots. Such flexible data criteria permit the assay designer to set a high degree of confidence with a minimum of data readings. Accordingly, the test system 70 operates at high degree of efficiency and accuracy as compared to known systems.

As noted above, the testing method also permits setting the data criteria to depend on assay test results or other biological-based criteria. In that circumstance, the comparison could be set to accept a sample if the results of an assay indicate that a particular genotype, for example, has a high probability (greater than 50%, 60%, 70%, 80%, 90% or greater depending upon the test and genotype and other variables), and to continue with acquiring data if the genotype is still uncertain.

Once the data criteria have been met, a "YES" outcome at block 75, the results are stored in block 76, such as in a database, and the instrument adjusted to move to the next sample in block 77. Accordingly, a new sample is selected in block 72.

If the data criteria have not yet been met, a "NO" outcome at block 75, then block 78 asks if there are any remaining spots on the sample. If unshot spots exist, a "NO" outcome at block 78, the instrument is adjusted in block 79 to acquire data from a new spot, and the data are acquired from the same sample at the new spot in block 73. If the data criteria are not met, "NO" at block 75, and there are no unshot spots, a "YES" outcome at block 78, then that particular sample is rejected, and the test moves on to a new sample at block 72.

Figure 5:
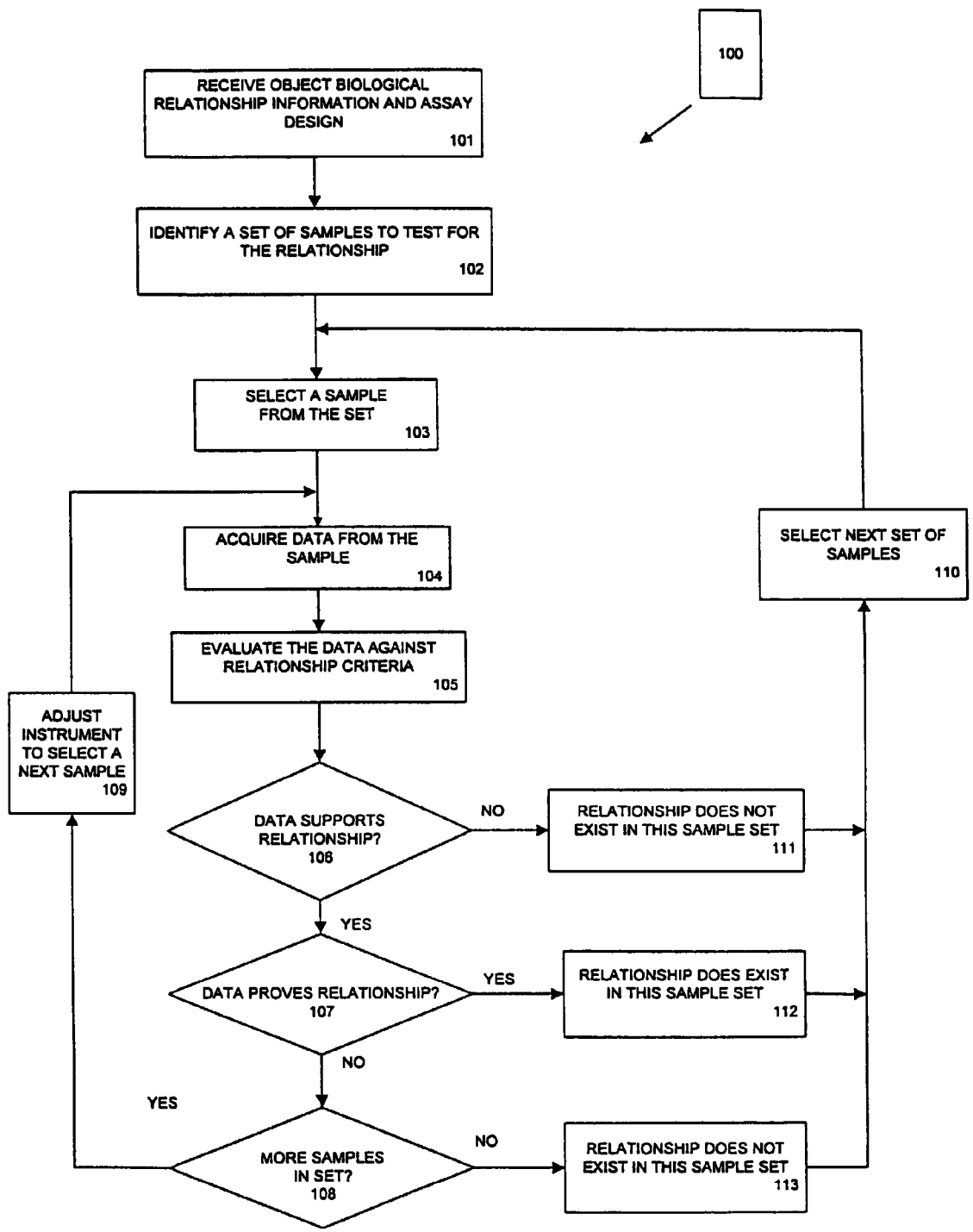
FIG. 5 is a flowchart of a testing process that illustrates acquiring data from multiple samples to establish the presence of a biological relationship.

Referring now to FIG. 5, a diagnostic testing method 100 is exemplified. The diagnostic testing method is directed to finding a relationship among a set of samples that proves a particular biological relationship exists. For example, certain clinical diagnostics can look at multiple samples from an individual before identifying that the individual is at risk for a particular disease, such as cystic fibrosis, where identification of multiple markers is needed for a diagnosis to be made. The diagnostic testing provided herein permits a clinical diagnosis at a high level of certainty and at a high level of efficiency, such as those using mass spectrometry-based systems.

The diagnostic testing method 100 receives an assay design and relationship criteria at block 101. The relationship criteria define the range of values and certainties where a relationship can be identified. In an exemplary embodiment, a relationship is the likelihood or risk that a particular individual will contract a particular disease. Since the accuracy of such assessment has serious consequences, it is crucial that such an identification be made only under the most confident conditions. Accordingly, known systems have required redundancies and over-testing to build confidence sufficient to make such a drastic announcement regarding an individual's health.

In block 102, a set of samples is identified for testing for the relationship. As there can be several, even tens of hundreds of samples to test, the set of samples can be present on multiple supports. Thus the testing method 100 should account for instructing an operator or a robot to deliver and load different supports as needed.

A particular sample is selected from the set in block 103, and data are acquired from the sample in block 104. The acquired data are evaluated against the relationship criteria in block 105. In an exemplary embodiment, testing system 10 (FIG. 1) incorporates aspects of the previously discussed testing method 70 to increase the confidence that the results from an individual sample are robust. The previously discussed method of over-sampling (rastering) a single biological sample can dramatically increase the confidence in the data from a single sample.

In block 106, the acquired data are evaluated to determine if it supports the object relationship. If the data does not support the object relationship, a "NO" outcome, then it is reported that the relationship does not exist in the set in block 111, and the test moves on to the next set of samples in block 110. Due to the high degree of confidence in sample results, it is possible for the testing method 100 to reject the entire sample and move to the next set. Accordingly, the testing method 100 can operate efficiently.

If block 106 finds that the data does support the relationship, a "YES" outcome, then block 107 asks if the data acquired thus far conclusively proves the relationship exists in accordance with the predefined criteria. If enough data has been collected, and the relationship proved, a "YES" outcome at block 107, then block 112 reports that the relationship exists, and the test moves on to the next set of samples. Thus, the testing method 100 only takes the necessary number of data acquisitions to call a diagnosis, enabling efficient operation.

If block 107 finds that the collected data does not prove the biological relationship, a "NO" outcome, then block 108 asks if there are any more samples to be tested in the sample set. If no more samples exist, a "NO" outcome at block 108, then block 113 reports that the relationship could not be proved, and the test moves on to the next sample set at block 110. If there are more samples to be tested, a "YES" at block 108, then the instrument is adjusted to the next sample in block 109, and data are acquired from the new sample in block 104.

FIG. 6 shows an example user display 130 for a test system. The user display 130, for example, can be presented on a computer monitor connected to an IBM compatible computer system, such as the workstation 12 and display 16 shown in FIG. 1. In an exemplary embodiment, the user display 130 is presented using a Microsoft® Windows® compatible display program, such as an application program provided herein and that is installed on the workstation 12.

The user display 130 has a spectrum window 132 for displaying a data spectrum of the most recently acquired data set. The spectrum window 132 enables an operator to watch, in near real-time, the data collected by the instrument. If multiple spots are shot for a particular sample, each successive data spectrum can be displayed in a different color so variations between spots is easily identified.

The user display also has a support representation window or frame 134. The support representation of FIG. 6 shows individual sample wells in a microtiter plate. For example, a well representation shows the wells in a physical microtiter plate support. As each well is tested, the well representation turns a different color base on whether the sample was accepted or rejected. A results display 138 shows assay data and a results quality display 140 shows run data for data sets. Accordingly, as the test progresses, an operator can identify certain systemic problems. For example, if all wells in a particular column fail, then there can be a problem with the syringe used to fill that particular column.

The information provided in the results display 138 can include a column of information containing a well identification number for each well of a sample plate or chip, along with an assay identification number that identifies the assay profile for the corresponding well. The information can also include, for example, in a genotyping assay, a genotype outcome column and a status column. The status column can be designed to indicate the degree of confidence with which the outcome, such as a genotype outcome, is made, if applicable. The status is typically indicated with a "conservative" indication, meaning a high level of confidence in the genotype call, or an "aggressive" indication, meaning low confidence in the genotype call. Other status indicators can indicate a moderate level of confidence or data that is insufficient to make a genotype call within the levels specified by system setup parameters.

The user interface 130 also has a sample view 136 which shows a live image of the sample tested. With this view, an operator can visually identify spots that have been used within a particular sample. Also, the operator can be able to identify certain systemic problems, such as a too small sample deposited into certain wells.

4. Assay-Based Judging Feedback for Modification of Data Acquisition and/or Analysis Assay-based judging provides numerous advantages in high throughput formats and, particularly, in multiplex assays formats. In light of the disclosure herein, those of skill in the art can envision a variety of such advantages. The performance metric tracked is whether an individual assay in a test gives acceptable performance. If it does not, it is not used in the criteria for the rest of the run. The criteria include, for example, acceptable genotyping, or allele frequency determination, or support of a diagnostic conclusion. Another criterium can be success of a group of assays that support a diagnostic conclusion. For example, if five assays are needed to support the conclusion, and it is determined that one has failed the other four might not be run, even if those are good.

As an example, the performance of a particular assay that is performed a plurality of times in a run can be used as a heuristic guide to the processor. If an assay or set of assays fails on a particular sample, the failure can indicate a problem with the assay or with the processing of that sample, or the problem can extend to all samples in the sample set. If the problem exists for all samples in the set, the failed assay can be removed from the determination of success or failure for the set of criteria used to evaluate the success or failure of the sample measurement. Hence when measuring a set of samples using assays that are common to more than one of the samples in the set, a failed assay can be removed. As a result, the throughput speed of the system is improved by using assay performance history to determine if additional data should be collected for a particular assay.

Figure 8:
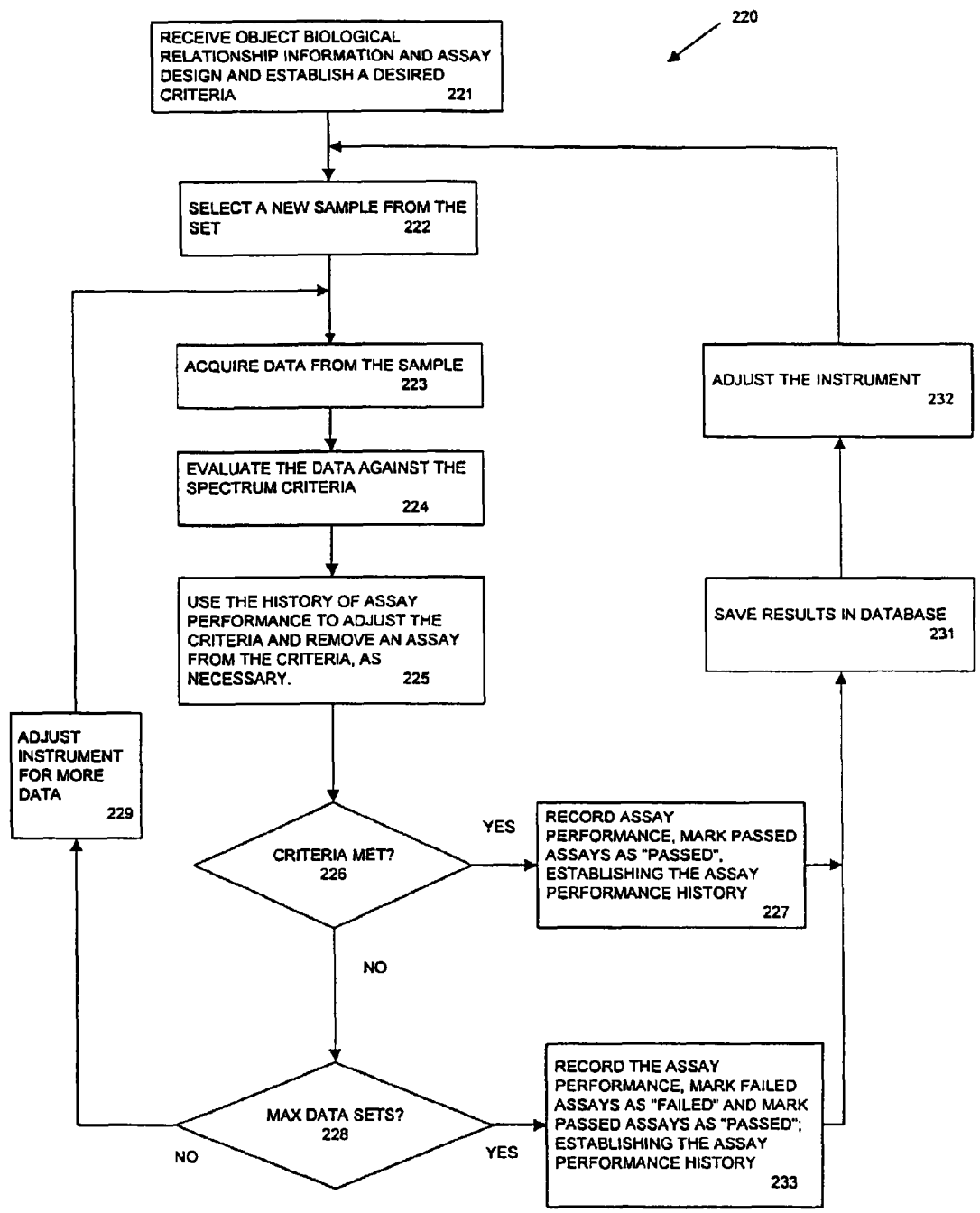
FIG. 8 is a flowchart that illustrates another embodiment of the assay-based judging processes provided herein in which performance history is assessed and increase throughput speed.

FIG. 8 is a flowchart that illustrates another embodiment of the assay-based judging methods (see, e.g., FIG. 4 and description thereof; see also the EXAMPLES) provided herein. In the embodiment depicted in FIG. 8, performance history based on assay outcome is evaluated and used to modify data acquisition.

In block 225, the system uses the assay performance history to adjust the criteria. The system does this by keeping statistics on the performance of all assays that are run on a set of samples. If an assay fails to provide an acceptable determination (for example, no genotype determination) for a succession of samples, then the system removes that assay from the criteria used to determine if more measurements on a sample are necessary. The number of times an assay can fail before removal from the criteria can be adjusted through user input, through the programming user interface of the workstation application program. Such number is predetermined; and is a function of the assays performed, samples and other parameters as needed. It should be noted that the results of assays that have failed continue to be calculated and stored in a results database. In an exemplary embodiment, if the assay begins to give good results, then the assay is returned to the set of criteria that is used to determine if additional data acquisition is needed and to control the data acquisition. In this way, use of assay performance history improves the efficiency of the test system.

With the evaluation criteria selected at block 225, the system determines if the data collected from the instrument meet the criteria at block 226. If the criteria is met, a "YES" outcome at block 226, then at block 227 the acquired data are recorded, including an assay performance record. An assay that provides a successful result is marked in the performance history as "passed". The acquired data and performance history record are recorded into a results database at block 231. At block 232 the instrument is adjusted for acquiring data from a new sample.

If the evaluation criteria are not met from a sample, a "NO" outcome at block 226, then at block 228 the system checks to determine if the maximum number of data sets have been acquired from the sample. The maximum number specifies a limit on the number of raster attempts that is performed on a single data sample in an attempt to get a successful outcome for all assays. If the maximum number of data sets has been reached, a "YES" outcome at block 228, then the system marks the failed assays as "failed" and marks any passed assays as "passed", at block 233. The system then records the acquired data and performance history in the database at block 231 and then adjusts the instrument for more data at block 232. If the maximum number of data sets has not been reached, a "NO" outcome at block 228, then at block 229 the system adjusts the instrument to acquire additional data from the sample (i.e., the system rasters the sample).

FIG. 8 thus shows an embodiment, in which in a multiplexed reaction, such as one in which 5 assays are run on 384 samples, the system can identify a failing reaction. The system starts at the first locus, and can be designed so that if the same reaction is failing after a predetermined number of loci, it stops rastering for that reaction in all of the remaining samples. Thus, the system can learn that a reaction is failing and take it out of the criteria. This speeds up the processing of the remaining samples. For example, if four out of five of the reactions run well, but a fifth does not, the system can eliminate the fifth from consideration in all samples once the failure is detected.

The following examples are included for illustrative purposes only and are not intended to limit the scope of the invention.

The following examples and the above detailed description depict application of the methods and systems (and comparison with prior systems) using mass spectrometry. It is understood that mass spectrometers and mass spectrometry are exemplary of instruments and output methods that can be employed in assay based judging systems and methods as provided herein. The medium, such as a microtiter plate, for testing in a particular instrument, can be adapted for a particular instrument, and include support for retaining or containing molecules and samples containing molecules. For high throughput formats, such supports are generally addressable and contain addressable loci, such as positionally addressable target (flat) loci or wells.

EXAMPLE 1

Comparative example setting forth steps in prior processes in which the data acquisition component (data collection routine(s)) and the biological calling component (data processing routine) are not integrated as provided herein (see, e.g., International PCT application Nos. WO 00/60361 and WO 02/25567):

A. First, obtain the data:
1. Place a support, such as a chip, or target with one or more samples on it into the data acquisition instrument, such as a mass spectrometer;
2. Get a locus list, such as a well list, from the user; this related to the support used or a set of assays it is just a list of the loci, such as wells, to run. The list of loci (i.e. wells) includes the calibrant loci (wells); they are not distinguished as different from the other loci they be run and the raw data are saved in the same way the data obtained from other loci are saved.
3. The user adjusts the geometry manually by centering one or more loci on a mark on the screen.
4. Collect the data.
   a. Go to the next locus (the first locus on the first time through this loop);
   b. Measure a raw mass spectrum;
   c. Examine the mass spectrum to see if there are any peaks in a fixed mass range;
   d. If there are peaks save the raw spectrum in a file and go back to step a;

e. If there are no peaks raster to a new spot on the sample and go back to step b;

The above loop saves the first "good" raster on each sample. Where "good" means that using a simple criteria (not biology based) that the mass spectrum had a peak that had good signal to noise somewhere in a fixed mass range window. After this data collection loop is run on a mass spectrometer, the system has a directory full of raw mass spectrum files; there are no biological results calculated.

B. Then, separately calculate the biological results (genotypes, allele frequencies, etc.)
  1. Copy the raw mass spectrum files from the mass spectrometer to a workstation configured for data processing;
  2. Get a list of assays for each sample from the database. There can be one or more assays for each sample. If there is more than one assay assigned to a sample this is referred to as a multiplex;
  3. Now calculate the assays results;
    a. First get the raw files which were measure from calibration wells and calibrate the mass range
    b. For each spectrum file do the following:
      i. Get the assay information for this spectrum and calculate the results of each assay represented by this spectrum.
      ii. Store the assay results in a database When performing high throughput assays this way, there is no assay information used while running the data acquisition instrument, such as a mass spectrometer. There are no biology based results calculated, displayed, nor are such results used to control the data acquisition instrument, such as a mass spectrometer, while it is running. Using the biology based results to control the data acquisition instrument, such as a mass spectrometer, an improvement data quality is observed.

Another difference is that when running the methods and using the systems provide herein (see, e.g., EXAMPLES 2 and 3), the system "knows" if there are multiple assays to measure on a sample and it treats each assay independently so it is possible to end up with a different spectra for each assay in a well. This can happen, for example, if the first assay is measured with high quality (conservative) on the first raster but other assays need more rasters to get a high quality results. The first assay has spectra generated from the first raster saved in the database as the raw data for this assay. The other assays for this sample have a different spectra that are a combination of subsequent rasters that give a high quality result.

When doing where the data acquisition and biological calling are not integrated, there is only one spectra per sample because the system does not know there are multiple assays to measure when it is collecting the data.

EXAMPLE 2

In contrast to method and system described in EXAMPLE 1, the following is an exemplary test process for the RT operation, such as that depicted in FIG. 4 (see, also FIG. 8 for another embodiment).
  1. Place a support, such as a chip or target with one or more samples on it into a mass spectrometer;
  2. Start the run;
  3. Get a list of samples from the database; and
  4. Get a list of assays for each sample from the database. There can be one or more assays for each sample. If there is more than one assay assigned to a sample this is referred to as a multiplex.
  5. Instruct the mass spectrometer to move to a set of samples (one or more) and use the sample visualization system, the framegrabber, and the image processing system to determine the position offset from the ideal target grid. This offset from ideal position is used to correct for geometry tolerance in the target and mechanical stage. Each time the mass spectrometer is instructed to move to a new sample this offset is included in the position of the new sample so that the target is positioned accurately with the sample lined up with the laser.
  6. Instruct the mass spectrometer to move to one or more calibration samples. Use the calibration data to calibrate the mass scale of the system.
  7. Now start to measure the samples
    A. Move to the next sample in the list (the first time through this is the first sample
    B. Now do the following steps repetitively until satisfactory results are achieved for each assay in the list of assays for this sample:
      i. Measure the sample.
      ii. Evaluate each assay in the list of assays for this sample and calculate a biology based result. This result can be a genotype, an allele frequency, etc.
      iii. If any assays in the list do not give a satisfactory result move to a new spot on the same sample—this small motion is called rastering—and measure the sample again.
      iv. Take the new data and the previous data and add the two spectra together. Now evaluate each assay that did not give satisfactory results previously again. If the result for these assays is improved by the new data then keep the new data which is the sum of previous measurements. Note: At this point we have results of one or more measurements on the sample. We can look at this set of measurements in a number of ways. In the current embodiment these measurements are summed if there is an improvement due to summing. The measurements could also be looked at individually and the best could be picked.
      v. If we have not measured the maximum number of raster positions on this sample then go back to step iii. The maximum number of raster positions is a parameter of the user interface.
      vi. Save the results for all assays failed or not
      vii. Display the result on the same user interface that is used to control the machine. The result is displayed in terms of the biological assay or assays that are performed.
    C. Go back to step A to get the next sample and continue until all samples are processed.

EXAMPLE 3

A Bruker Biflex instrument was modified to include real-time genotype calling capabilities as provided herein. The modifications included the addition of a PC workstation equipped with a Signatec PDA500 500 MHz 8-bit digitizer and a National Instruments IMAQ-PCI 1411 frame grabber. Four signals were disconnected from the Biflex and routed to the PC Workstation. These signals are: the output of the MCP detector, the trigger for the laser and high voltage electronics, the output of a photo diode detector used to trigger the data acquisition, and the video signal from the sample visualization camera. The output of the detector in the Biflex passed through a gain of five pre-amplifier (Stanford Research Systems SR445) and a passive low pass filter with a cutoff frequency of 90 MHz (Mini Circuits BLP-90). In addition, there was a TCP/IP connection between the PC workstation and the controlling computer on the Biflex (Sun workstation).

The software on the Sun workstation was modified to accept commands over the TCP/IP interface to move the stage from sample-to-sample and to different raster positions within a sample. The workstation was equipped with software that triggers the mass spectrometer (laser and high voltage pulsing) and acquires the spectrum. The software also controls stage position.

The software that was incorporated into the system can control the mass spectrometer and acquire spectra and process these spectra in real-time. The biology based results are used to decide whether or not to raster. The software uses the following algorithm. A set number of shots determined by a parameter are averaged to create a spectra. Each assay defined for that sample is judged independently. If the score for an assay is less than moderate then the system collects more data for that assay. Another set of shots is averaged and the result of this data collection is added to the first. Again, a result for each assay is determined and if the score for that assay improves by adding the new shots, the new sum is kept. The process continues until a set number of attempts has expired or a score of moderate or better is achieved for each assay in the sample. It is possible that each assay in the well ends up with a different spectra.

Figure 9:
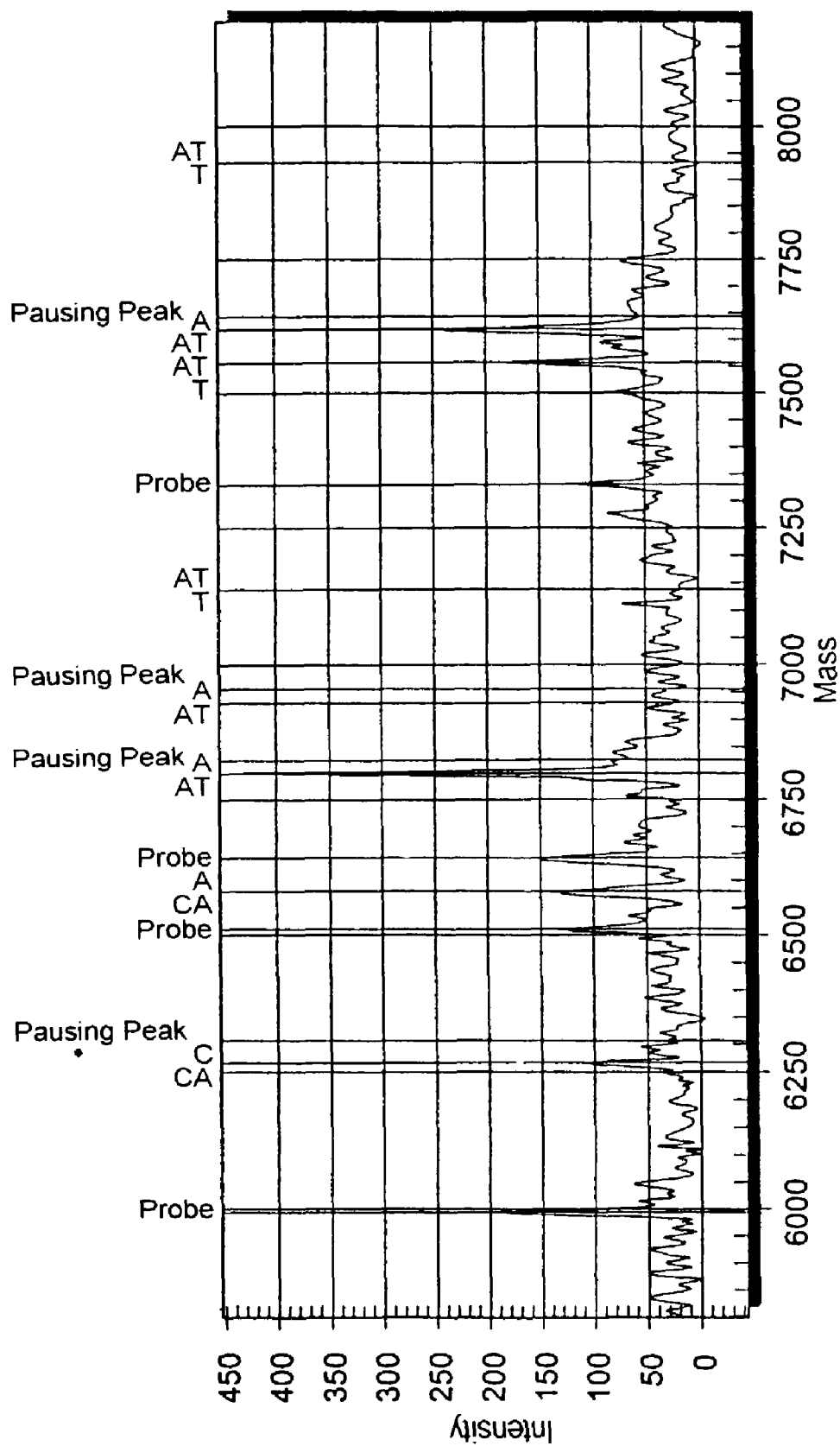
FIG. 9 is a diagram that shows an exemplary mass spectrum acquired and data outcome from data acquisition using prior methods without the biology-dependent rastering control (assay-based judging).
Figure 10:
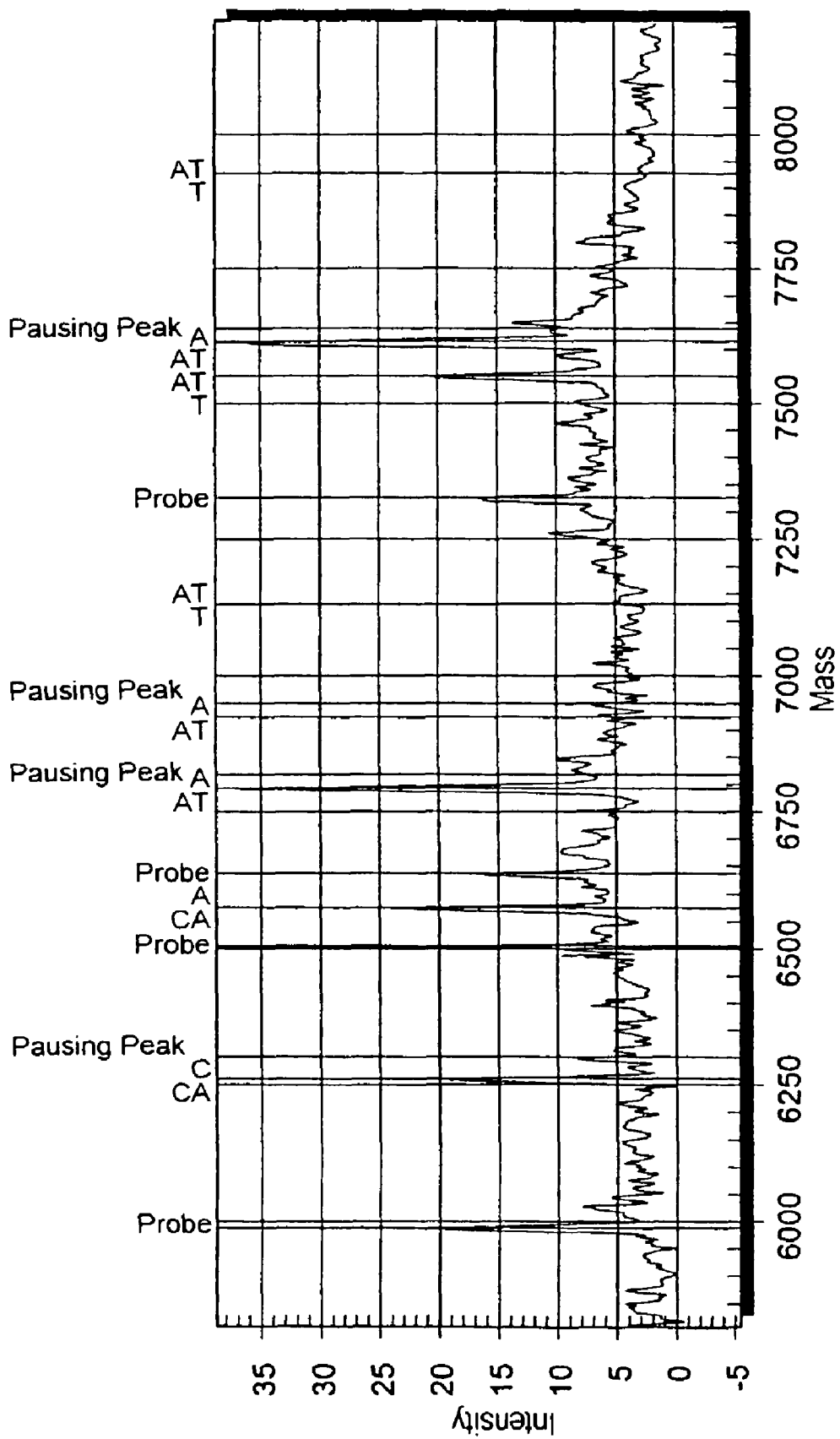
FIG. 10 is a diagram that shows a mass spectrum acquired and data outcome from data acquisition using the biology-dependent rastering control (assay-based judging) as provided herein.

In a typical experiment, 48 new non-established (this was the first run for each of these assays) 4-plexes were performed on eight different DNA's (384 reactions) and spotted on a 384 chip. The same 384 chip was measured consecutively on three different Biflex instruments. The first run was performed using the standard Biflex Autoxecute software. The standard acquisition available with the Biflex uses fuzzy logic to control rastering based on resolution and signal to noise ratio over a fixed mass range. The next two runs were performed on Biflex instruments equipped as provided herein. Normally the quality of the data would decrease in consecutive runs because the sample is depleted by successive laser shots. The results are presented in Table 1, FIG. 9 and FIG. 10). FIG. 9 is a diagram that shows the spectra acquired and data outcome from data acquisition without the assay-based rastering control provided herein. FIG. 10 is a diagram that shows the spectra acquired and data outcome from data acquisition using the biology-dependent rastering control provided herein FIG. 9 shows a spectrum that contains the results from four assays using the "standard" configuration instrument system in which data are processed without benefit of the assay-based judging described herein. The system made two conservative calls and two aggressive calls and found at least one peak of sufficient quality to use this spectra output and move to the next sample. In contrast, using assay-based processing provided herein showed that the data was not sufficient to provide the desired four, high-quality genotyping results. As a result, additional data acquisition resulted in four conservative calls, as illustrated in FIG. 10.

Specifically, FIG. 9 shows a spectra acquired by the Biflex using its standard judging algorithms. This spectrum contains the results for four assays. In this case, the data resulted in two conservative calls and two aggressive calls. As can be seen, the spectra is complex and the simple judging employed by the Bruker found at least one peak of sufficient quality to save this spectra and move on. FIG. 10 shows the spectra acquired using assay based judging. In this case, the data resulted in four conservative calls. FIG. 10 depicts spectra acquired using real-time genotyping to control the acquisition. 48 new non-established (this was the first run for each of these assays) 4-plexes were performed on eight different DNA's (384 reactions) and spotted on a 384 chip. The same 384 chip was measured consecutively on three different Biflex instruments. The first run was performed using the standard Biflex Autoxecute software. The standard acquisition uses fuzzy logic to control rastering based on resolution and signal to noise ratio over a fixed mass range. The next two runs were performed on modified Biflex instruments. The modifications were as described in the experimental section above. Normally the quality of the data would decrease in consecutive runs because the sample is depleted by successive laser shots. The results are presented in the Table.

TABLE 1

| Call quality | Run 1 Standard configuration | Run 2 Assay based | Run 3 Assay based |
| --- | --- | --- | --- |
| Total possible calls | 1536 | 1536 | 1536 |
| Conservative calls | 1062 | 1310 | 1199 |
| Moderate calls | 121 | 86 | 167 |
| Aggressive calls | 90 | 5 | 23 |
| Low probability | 140 | 58 | 98 |
| Bad spectrum | 123 | 77 | 98 |
| Total "good" calls | 1183 | 1396 | 1366 |
| Improvement in efficiency over Standard configuration | N/A | 18% | 15.5% |

In the Table, a "good" call is defined as the total of conservative calls plus the moderate calls.

The results in Table 3 show that the call efficiency was improved by using assay-based judging in accord with the methods and systems provided herein to control data acquisition. In particular, overall call efficiency was improved from 77% for the "standard" configuration to 90.9% in the first data run using the assay-based judging.

Since modifications are apparent to those of skill in this art, it is intended that this invention be limited only by the scope of the appended claims.

What is claimed:

1. A system for performing biological assays in a multiplex format, comprising:
  a) a data acquisition instrument for detecting biopolymers in a sample or samples in a multiplex format, wherein said data acquisition instrument comprises a mass spectrometer;
  b) a data analysis processor integrated with said data acquisition instrument; wherein said data analysis processor determines the presence or absence of an object biological relationship from said acquired data, provides ultimate results-based control of said data acquisition instrument, wherein the system directs the instrument to obtain further data where the presence or absence of the object biological relationship is not determined, and said data acquisition instrument can be adjusted and directed by the processor based on the ultimate results to retest the sample at a different spot on the sample, or to retest the sample at an adjusted power setting, or to retest the sample at an adjusted measurement filter until the standard deviation of the biological results achieves a desired degree of certainty and the presence or absence of the object biological relationship is determined, or to proceed to another sample.

2. A system of claim 1, wherein said data acquisition instrument collects data from said sample or samples, said data analysis processor obtains an assay score for said data and directs said data acquisition instrument to re-test the sample to obtain additional data.

3. A system of claim 2, wherein said data analysis processor sums said additional data and said acquired data.

4. A system of claim 2, wherein said data analysis processor replaces said acquired data with said additional data.

5. A system of claim 1, wherein said system displays said object biological relationship in real time.

6. A system of claim 1, wherein integration is effected by a calling component that identifies a data result to make decisions regarding further data acquisition responsive to ultimate results.

7. A system of claim 6, wherein the processor comprises a programming interface that controls a dialog between the data acquisition instrument and the calling component.

8. A system of claim 1, wherein the data analysis processor
   a) establishes at least one data spectrum criterion based on a biological assay design;
   b) directs the data acquisition instrument to acquire data indicative of the biological sample;
   c) generates a data spectrum using the acquired data;
   d) compares the data spectrum to the at least one data spectrum criterion;
   e) adjusts the data acquisition instrument responsive to the data comparison; and
   f) directs the data acquisition instrument to acquire other data for the biological assay.

9. A system of claim 8, wherein the data analysis processor establishes the data spectrum criterion by generating a data spectrum criterion indicative of standard deviation for a characteristic of the acquired data.

10. A system of claim 8, wherein the data analysis processor establishes the data spectrum criterion by generating a data spectrum criterion indicative of statistical probability.

11. A system of claim 8, wherein the data analysis processor establishes the data spectrum criterion by generating a data spectrum criterion indicative of allele probability.

12. A system of claim 1, wherein said system further comprises a display that displays the data collected by said data collection instrument in real time.

13. A system of claim 1, wherein the data analysis processor further comprises a database, stores an assay design in said database, and directs said data collection instrument to acquire data in accordance with the assay design.

14. A system of claim 13, wherein the data analysis processor uses the assay information from said database to calculate the adjustment of the data collection instrument.

15. A system of claim 1, wherein the data analysis processor is configured as a computer device coupled to the instrument.

16. A system of claim 1, wherein the data analysis processor comprises a data processing routine to determine a diagnosis.

17. A system of claim 1, wherein the data analysis processor comprises a data processing routine to determine a genotype.

18. A system of claim 1, wherein the data analysis processor comprises a data processing routine to determine an allelic frequency.

19. A system of claim 1, wherein the data analysis processor comprises a data processing routine to determine a risk of developing a disease or condition.

20. A method for performing biological assays, comprising:
   a) introducing a sample into the system of claim 1; and
   b) acquiring data from said sample and determining the ultimate result of said acquired data.

21. A method of claim 20, wherein the data analysis processor
   a) establishes at least one data spectrum criterion based on a biological assay design;
   b) directs the data acquisition instrument to acquire data indicative of the biological sample;
   c) generates a data spectrum using the acquired data;
   d) compares the data spectrum to the at least one data spectrum criterion;
   e) adjusts the data acquisition instrument responsive to the data comparison; and
   f) directs the data acquisition instrument to acquire other data for the biological assay.

22. A method of claim 20 wherein said system saves the assay result in a database.

23. A method of claim 20 where in said system displays the biological assay result on a user interface.

24. A method of claim 20, wherein the object biological relationship is a determination of risk of developing a disease or condition.

25. A method of claim 20, wherein the object biological relationship is a diagnosis.

26. A method of claim 20, wherein the object biological relationship is a genotype.

27. A method of claim 20, wherein the object biological relationship is an allelic frequency.

28. The method of claim 20, further comprising
   a) introducing a solid support containing one or a plurality of samples into said mass spectrometer; and
   b) for one or more samples, measuring the sample by performing at least one assay on said sample and calculating a data spectrum.

29. A method of claim 28, wherein
   a) the data analysis processor establishes at least one data spectrum criterion based on at least one biological assay design;
   b) compares said data spectrum to the at least one data spectrum criterion; and
   c) if the data spectrum does not meet the data spectrum criterion, and the maximum number of a predetermined number of raster positions has not been measured, the data analysis processor directs the data acquisition instrument to measure the sample at another raster position on the solid support.

30. A method of claim 29 wherein said system saves the assay results in a database.

31. A method of claim 30, wherein said system saves the history of the assay results in a database.

32. A method of claim 31, wherein more than one data spectrum criterion is established and said data analysis processor removes or adds assays from the data spectrum criterion.

33. A method of claim 32, wherein said data analysis processor uses the history of the assay results in said database to determine whether to remove or add an assay from the biological assay result criteria.

34. A method of claim 20, wherein the object biological relationship is selected from the group consisting of a determination of risk of developing a disease or condition, a diagnosis, a genotype, or an allelic frequency.

35. A method for performing biological assays, comprising
   a) introducing a solid support containing one or a plurality of samples into the instrument of a system of claim 1, wherein said data acquisition instrument is a mass spectrometer; and
   b) acquiring data from said sample and determining the object biological relationship of said acquired data.

36. A system of claim 1, wherein the object biological relationship is selected from the group consisting of a determination of risk of developing a disease or condition, a diagnosis, a genotype, or an allelic frequency.

* * * * *